(12) United States Patent
Chen

(10) Patent No.: US 11,090,330 B2
(45) Date of Patent: Aug. 17, 2021

(54) PHARMACEUTICAL SOLUTION HAVING A TOXICITY-REDUCING EFFECT FOR ANTITUMOR DRUGS, AND PHARMACEUTICAL COMPOSITION COMPRISING SAME

(71) Applicant: Songyuan Chen, Guangzhou (CN)

(72) Inventor: Songyuan Chen, Guangzhou (CN)

( * ) Notice: Subject to any disclaimer, the term of this patent is extended or adjusted under 35 U.S.C. 154(b) by 0 days.

(21) Appl. No.: 16/407,736

(22) Filed: May 9, 2019

(65) Prior Publication Data

US 2019/0262267 A1   Aug. 29, 2019

Related U.S. Application Data

(63) Continuation-in-part of application No. 15/360,065, filed on Nov. 23, 2016, now abandoned, which is a
(Continued)

(30) Foreign Application Priority Data

May 26, 2014   (CN) .......................... 201410227737.7

(51) Int. Cl.
    *A61P 35/00*     (2006.01)
    *A61K 9/00*      (2006.01)
    (Continued)

(52) U.S. Cl.
    CPC ............ *A61K 33/00* (2013.01); *A61K 9/0019* (2013.01); *A61K 9/08* (2013.01); *A61K 9/10* (2013.01); *A61K 31/282* (2013.01); *A61K 31/407* (2013.01); *A61K 31/505* (2013.01); *A61K 31/675* (2013.01); *A61K 31/7068* (2013.01);
    (Continued)

(58) Field of Classification Search
    None
    See application file for complete search history.

(56) References Cited

U.S. PATENT DOCUMENTS 4,604,286 A * 8/1986 Kawajiri ................ A61K 33/42
                                                          424/601
4,975,423 A * 12/1990 Gaffar ................... A61K 33/42
                                                          424/601
(Continued)

FOREIGN PATENT DOCUMENTS

CN   101292742 A   10/2008
CN   101757158 A    6/2010
(Continued)

OTHER PUBLICATIONS

HJ Altermatt, J-O Gebbers, JA Laissue. "Heavy Water Enhances the Antineoplastic Effect of 5-Fluoro-Uracil and Bleomycin in Nude Mice Bearing Human Carcinoma." International Journal of Cancer, vol. 45, 1990, pp. 475-480. (Year: 1990).*

(Continued)

*Primary Examiner* — Isaac Shomer
(74) *Attorney, Agent, or Firm* — Meunier Carlin & Curfman LLC

(57) ABSTRACT

The present disclosure relates to a pharmaceutical solution having a toxicity-reducing effect for anti-tumor drugs, and a pharmaceutical composition comprising the solution as well as a method for using them. The pharmaceutical solution uses deuterium oxide as a solvent.

12 Claims, 5 Drawing Sheets

Related U.S. Application Data continuation-in-part of application No. PCT/CN2015/079686, filed on May 25, 2015.

(51) Int. Cl.

| | | |
|---|---|---|
| *A61K 9/08* | (2006.01) | |
| *A61K 9/10* | (2006.01) | |
| *A61K 47/02* | (2006.01) | |
| *A61K 47/10* | (2017.01) | |
| *A61K 47/18* | (2017.01) | |
| *A61K 47/26* | (2006.01) | |
| *A61K 47/40* | (2006.01) | |
| *A61K 33/243* | (2019.01) | |
| *A61K 31/282* | (2006.01) | |
| *A61K 31/407* | (2006.01) | |
| *A61K 31/505* | (2006.01) | |
| *A61K 31/675* | (2006.01) | |
| *A61K 31/7068* | (2006.01) | |
| *A61K 39/395* | (2006.01) | |
| *A61K 33/00* | (2006.01) | |
| *A61K 45/06* | (2006.01) | |

(52) U.S. Cl.
CPC ........ *A61K 33/243* (2019.01); *A61K 39/3955* (2013.01); *A61K 47/02* (2013.01); *A61K 47/10* (2013.01); *A61K 47/183* (2013.01); *A61K 47/26* (2013.01); *A61K 47/40* (2013.01); *A61P 35/00* (2018.01); *A61K 45/06* (2013.01)

(56) References Cited

U.S. PATENT DOCUMENTS

| | | | |
|---|---|---|---|
| 6,683,100 B2 * | 1/2004 | van Hoogevest | A61K 9/0019 514/365 |
| 2013/0142724 A1 | 6/2013 | Wang | |
| 2013/0197212 A1 * | 8/2013 | Westphal | A61K 31/7068 536/111 |

FOREIGN PATENT DOCUMENTS

| | | |
|---|---|---|
| CN | 102274258 A | 12/2011 |
| CN | 102274259 A | 12/2011 |
| CN | 102369012 A | 3/2012 |
| WO | 9603996 A1 | 2/1996 |
| WO | 9740841 A1 | 11/1997 |
| WO | 2006022460 A1 | 3/2006 |
| WO | WO-2006022460 A1 * | 3/2006 ........... A61K 9/0034 |
| WO | WQ-2006022460 A1 * | 3/2006 ............. A61K 31/40 |
| WO | 2010079420 A1 | 7/2010 |

OTHER PUBLICATIONS

M Yokoo et al. "Antiproliferative Effect of 2-Hydroxypropyl-b-Cyclodextrin (HP-b-CyD) Against Chronic Myeloid Leukemia In Vitro and In Vivo." Blood (2012) 120 (21): 2442, 7 printed pages. (Year: 2012).*

Dietrich Bosse, Michaela Praus, Peter Kiessling, Lars Nyman, Corina Andresen, Joanne Waters, and Fritz Schindel. "Phase I Comparability of Recombinant Human Albumin and Human Serum Albumin." Journal of Clinical Pharmacology, vol. 45, 2005, pp. 57-67. (Year: 2005).*

Raymond C. Rowe, Paul J. Sheskey, and Marian E. Quinn. "Handbook of Pharmaceutical Excipients, Sixth Edition." Pharmaceutical Press, 2009, pp. i-xxviii and 1-888. (Year: 2009).*

Jessica Mitchell and Aminah Jatoi. "Parenteral Nutrition in Patients With Advanced Cancer: Merging Perspectives From the Patient and Healthcare Provider." Seminars in Oncology, vol. 38, No. 3, Jun. 2011, pp. 439-442. (Year: 2011).*

J Hartmann et al. "Effects of Heavy Water (D2O) on Human Pancreatic Tumor Cells." Anticancer Research, vol. 25, 2005, pp. 3407-3412. (Year: 2005).*

Luca Goldoni, Mario Grugni, Sergio De Munari, Mara Cassin, and Raffaella Bernardini. "Cucurbit[7]uril Inclusion Complexes of Platinum(II)-based Anticancer Drugs: Further Insight." Chemistry Letters, vol. 39, 2010, pp. 676-677. (Year: 2010).*

Ulf Olsson, Kozo Shinoda, and Bjorn Lindman. "Change of the Structure of Microemulsions with the Hydrophile-Llpophile Balance of Nonionic Surfactant as Revealed by NMR Self-Diffusion Studies." The Journal of Physical Chemistry, vol. 90, No. 17, 1986, pp. 4083-4088. (Year: 1986).*

Lik-Voon Kiew, Soon-Keng Cheong, Khalifah Sidik, Lip-Yong Chung. "Improved plasma stability and sustained release profile of gemcitabine via polypeptide conjugation." International Journal of Pharmaceutics, vol. 391 (2010) 212-220. (Year: 2010).*

John E. Hanson. "Chapter 5 NMR Spectroscopy in Nondeuterated Solvents (No-D NMR): Applications in the Undergraduate Organic Laboratory." Obtained from https://pubs.acs.org/doi/pdf/10.1021/bk-2013-1128.ch005?rand=0xfzreet on Jan. 28, 2021, originally published 2013, pp. 69-81. (Year: 2013).*

Dorice M. Czajka, Asher J. Finkel, Conrad S. Fischer, and Joseph J. Katz. "Physiological effects of deuterium on dogs." American Journal of Physiology, vol. 201, Issue 2, Aug. 1961, pp. 357-362. (Year: 1961).*

Jean A. Laissue, Heinz Burki, and Willi Berchtold. "Survival of Tumor-bearing Mice Exposed to Heavy Water or Heavy Water plus Methotrexate." Cancer Research, vol. 42, Mar. 1982, pp. 1125-1129. (Year: 1982).*

Extended European Search Report dated Oct. 25, 2017 for counterpart European application No. 15799410.4.

International preliminary examination report dated Sep. 30, 2016 for counterpart Chinese patent application No. PCT/CN2015/079686.

International Search Report dated Aug. 19, 2015 for counterpart Chinese patent application No. PCT/CN2015/079686.

"Chemicals Known to the State to Cause Cancer or Reproductive Toxicity", State of California Environmental Protection Agency, Office of Environmental Health and Hazard Assessment, Safe Drinking Water and Toxic Enforcement Act of 1986, May 11, 2015.

Allen, et al., "Influence of Deuterium Oxide on Calcium Transients and Myofibrillar Responses of Frog Skeletal Muscle", J. Physiol, 354, 1984, 225-251.

Altermatt, Hans J. et al., "Heavy Water Delays Growth of Human Carcinoma in Nude Mice", Cancer vol. 62, 1988, 462-466.

Altermatt, Hans J. et al., "Heavy Water Enhances the Antineoplastic Effect of 5-Fluoro-Uracil and Bleomycin in Nude Mice Bearing Human Carcinoma", Int. J. Cancer vol. 45, 1990, 475-480.

Bader, et al., "Synergistic effects of deuterim oxide and gemcitabine in human pancreatic cancer cell lines", Cancer Letters vol. 259, No. 2, Feb. 2, 2008, 231-239.

Bahk, et al., "Anticancer Effect of Dueterium Oxide on a Bladder Cancer Cell Related to Bcl-2 and Bax", J. Ind. Eng. Chem. vol. 13, No. 4, 2007, 501-507.

Czajka, et al., "Physiological effects of deuterium on dogs", Divisions of Biological and Medical Research, Health, and Chemistry, Argonne National Laboratory, Argonne, Illinois, 1961, 357-362.

Czajka, Dorice M. et al., "Effect of Deuterium Oxide on the Reproductive Potential of Mice", Annals of the New York Academy of Sciecnes, vol. 84(16), 1960, 770-779.

Gross, et al., "Blockade of deoxyribonucleic acid synthesis by deuterium oxide", Abstract, Science, 133(3459), 1961, 1131-3.

Hartmann, Johannes et al., "Effects of Heavy Water (D2O) on Human Pancreatic Tumor Cells", Hartmann et al., Effects of Heavy Water (D2O) on Human Pancreatic Tumor Cells, Anticancer Research, vol. 25, pp. 3407-3412, 2005., 2005, 3407-3412.

Jeon, Young Jin et al., "Novel molecular drug carrier: encapsulation of oxaliplatin in cucurbit[7]uril and its effects on stability and reactivity of the drug", Jeon et al., Novel molecular drug carrier: encapsulation of oxaliplatin in cucurbit[7]uril and its effects on stability and reactivity of the drug, Org Biomol Chem., 3, pp. 2122-2125, 2005., 2005, 2122-2125.

(56) References Cited

OTHER PUBLICATIONS

Kameda, Jun et al., "Mechanisms of hydrogen generation during the mechanochemical treatment of biotite within D2O media", Kameda et al., Mechanisms of hydrogen generation during the mechanochemical treatment of biotite within D2O media, Earth Planets Space, vol. 56, pp. 1241-1245, 2004., 2004, 1241-1245.
Katz, Joseph J. , "Chemical and Biological Studies With Deuterium", American Scientist vol. 48(4), 1960, 544-580.
Laissue, , "Survival of Tumor-bearing Mice Exposed to Heavy Water or Heavy Water plus Methotrexate", Cancer Research vol. 42, 1982, 1125-1129.
Somlyai, Gabor et al., "Naturally occurring deuterium is essential for the normal growth rate of cells", Federation of European Biochemical Societies vol. 317, 1993.
Takeda Hiroshi, et al., "Mechanisms of cytotoxic effects of heavy water(deuterium oxide: D20) on cancer cells", Anti-Cancer Drugs, Lippincott Williams & Wilkins, US vol. 9, No. 8, Sep. 1, 1998, 715-725.
Uemura, Takeshi et al., "Experimental validation of deuterium oxide-mediated antitumoral activity as it related to apoptosis in murine malignant astrocytoma cells", Uemura et al., Experimental validation of deuterium oxide-mediated antitumoral activity as it related to apoptosis in murine malignant astrocytoma cells, J Neurosurg, 96, p. 900-908, 2002., 2002, 900-908.
Yokoo, Masako et al., "Antiproliferative Effect of 2-Hydroxypropyl-B-Cyclodextrin (HP-B-CyD) Against Chronic Myeloid Leukemia In Vitro and In Vivo", Yokoo et al., Antiproliferative Effect of 2-Hydroxypropyl-B-Cyclodextrin (HP-B-CyD) Against Chronic Myeloid Leukemia In Vitro and In Vitro, Bllod, vol. 120, 2442, 2012, 2012.
Database TCM [Online] SIPO; Jan. 22, 2008, Au Jixiu:"A kind of Radix Panacis Quinquefolii Flos Rosae Rugosae buccal Tablet", XP002756410.
Database WPI Week 200909 Thomson Scientific, London, GB; AN 2009-833845, XP002756409.
Database WPI Week 201220 Thomson Scientific, London, GB; AN 2012-A22891, XP002756408.
Database WPI Week 201219 Thomson Scientific, London, GB; AN 2012-A22889, XP002756407.
Extended European Search Report dated Jul. 23, 2019 for counterpart European patent application No. 19175214.6.
Yamaguchi N., et al., Augmentation of various immune reactivities of tumor-bearing hosts with an extract of Cordyceps sinesis, Biotherapy 2, vol. 2, No. 3, Jan. 1, 1990, pp. 199-206, XP001069490.
Guerrero-Analco J.A., et al., Bioactive Polysaccharides of North American Ginseng Panax quinquefolius L. in Modulation of Immune Function: Preliminary Chemical and Biological Characterization, Planta Medica, Thieme Verlag, DE, vol. 79, No. 10, Jul. 1, 2013, pp. 835-836, XP009189492.
Yue G.G.L. et al., Immunomodulatory Activities of Ganoderma sinense Polysaccharides in Human Immune Cells, Nutrition and Cancer, Routledge, US, vol. 65, No. 5, Jul. 1, 2013, pp. 765-774, XP009189488.
Yang Wei et al., Effects of Ganoderma lucidum essence powder and Ganoderma Lucidum spore powder on immune function of mice with Lewis lung cancer, Chinese Journal of Biologicals / Zhong Guo Sheng Wu Zhi Pin Xue Za Zhi, Chinese Preventive Medicine Association, China, vol. 25, No. 9, Sep. 1, 2012, 1171-1175, XP009189495.
Durairaj P, et al., Quantitative augmentation of immune cells in elderly normal mice by short-term, daily consumption of an extract of North American ginseng (Panax quinquefolius), Biomedical Research (I NOIA) 2013 Scientific Publishers of India Ind, vol. 24, No. 2, Mar. 20, 2013, pp. 199-205, XP009189493.
Decision of Rejection issued for corresponding Japanese Patent Application 2017-514768 dated Sep. 24, 2019.
Frontier, Treatment for peritoneal dissemination from colorectal cancer, vol. 6, No. 1, pp. 21-25, 2013.
Laissue et al., Survival of Tmor-bearing Mice Exposed to Heavy Water of Heavy Water plus Methotrexate, Cancer Research, vol. 42, pp. 1125-1129, 1982.
Altermatt et al., Heavy Water Enhances the Antineoplastic Effect of 5-Fluoro-Uracil and Bleomycin in Nude Mice Bearing Human Carcinoma, Int. J. Cancer, vol. 45, pp. 475-480, 1990.
English Translation of the Second Office Action dated Sep. 23, 2019 for counterpart Chinese patent application No. 201580027908.4, downloaded from the EPO.
English Translation of Chinese First Office Action and search report issued in CN 201580027908.4, dated Feb. 3, 2019.
English Translation of Japanese First Office Action issued in JP 2017-514768 dated Feb. 5, 2019.
Kameda et al., Mechanisms of hydrogen generation during the mechanochemical treatment of biotite within D2O media, Earth Planets Space, vol. 56, pp. 1241-1245, 2004.
English Summary of Treatment for peritoneal dissemination from colorectal cancer—Hyperthermin intra-peritoneal chemotherapy (HIPEC), Frontiers in Colorectal Cancer, vol. 6, No. 1, pp. 21-25, 2013.

* cited by examiner

PHARMACEUTICAL SOLUTION HAVING A TOXICITY-REDUCING EFFECT FOR ANTITUMOR DRUGS, AND PHARMACEUTICAL COMPOSITION COMPRISING SAME

CROSS-REFERENCE TO RELATED APPLICATIONS

This application is a continuation-in-part application of PCT/CN2015/079686 filed May 25, 2015, which claims priority to Chinese application number 201410227737.7 filed May 26, 2014.

TECHNICAL FIELD

The present disclosure belongs in the field of medicine, and relates to a pharmaceutical solution having an toxicity-reducing effect for antitumor drugs, and a pharmaceutical composition comprising the solution, as well as a method for using them.

BACKGROUND ART

At present, the one main therapies against malignant tumors is chemotherapy with various anti-tumor drugs, but which often certain severely toxicity. It is known that some tumor patients, particularly kids, women, and aged patients with liver disease, cannot bear the toxicity of anti-tumor drugs. But they still have to continue the administration of these anti-tumor drugs. They will suffer from a great pain caused by the anti-tumor drugs toxicity which can also cause severe vomiting, immune hypofunction, bacterial or viruses infections, and severe hepatopathy.

For example, a commonly used anti-tumor drug 5-fluorouracil (5-PU) shows severe vomiting, hepatopathy and loses body weight in clinical settings. And many anti-tumor drugs have same toxicity. Therefore to reduce their toxicity is an important strategy towards improvement of clinical efficacy of anti-tumor drugs.

The tumors are a large family of diseases that involve mutant genes in the cells, lead to unregulated cells growth fast with the potential to invade or spread to other parts of the body. But the cells in bone morrow and liver are normal cells in the same body, totally different to compare the tumor cells with the structure, pathophysiology, heterogeneity, micro-environment of cells. For example, there are mutant receptors on the tumor cell membrane, but no mutant receptors on the normal cell membrane. That is reason why the same substance has different function with different cells in the same subject. On the one hand, it kills tumor cells in the body, and on the other hand, it protects normal cells in bone morrow and liver in the same body.

Summary of the Disclosure

Deuterium oxide (heavy water, D2O, Mw: 20.03, CAS No. 7789-20-0) can be isolated from seawater. A normal body of adult human contains about 5 g deuterium oxide. It has been demonstrated by experiments using dogs as an animal model that exogenous deuterium oxide that reaches a concentration of 30% in the body causes a toxic effect.

The present disclosure is made based on the following findings by the inventor 1) deuterium oxide has an effect of toxicity-reducing for antitumor drugs.
2) use of deuterium oxide to dissolve or dilute other anti-tumor drugs to prepare various pharmaceutical solutions, and can apply various administration routes such as oral, intravenous injection or instillation, intra-arterial injection, transcatheter embolization, topical (such as thoracic cavity, peritoneal cavity, pelvic cavity, bladder cavity, rectal lumen, buccal and nasal cavity, uterine cavity, and skin) perfusion and lavage and 40° C.-48° C. hyperthermic perfusion and lavage.
3) toxicity reducing effect for anti-tumor drugs is obtained by dissolving or diluting of anti-tumors drugs in deuterium oxide, and by various administration routes such as oral, injection, or by topical (such as thoracic cavity, peritoneal cavity, pelvic cavity, bladder cavity, rectal lumen, buccal and nasal cavity, uterine cavity, articular cavity, and skin) perfusion, lavage and 40° C.-48° C. hyperthermic perfusion and lavage.
4) safety is achieved: administration of deuterium oxide by oral, direct injection, or by topical (such as thoracic cavity, peritoneal cavity, pelvic cavity, bladder cavity, rectal lumen, buccal and nasal cavity, uterine cavity, articular cavity, and skin) perfusion, lavage and 40° C.-48° C. hyperthermic perfusion and lavage is safe to mammals.

In summary, deuterium oxide per se has when administered in combination with various anti-tumor drugs, it can effectively attenuate the toxicity of these anti-tumor drugs, thereby useful for treatment of malignant tumors, which is an unexpected effect.

An aspect of the present disclosure is to provide a pharmaceutical solution characterized by using deuterium oxide as a solvent.

Another aspect of the present disclosure is to provide a medicament for combinational administration, characterized in that the medicament comprises the pharmaceutical solution of the present disclosure, at least one anti-tumor drug, and optionally one or more pharmaceutically acceptable excipients.

Another aspect of the present disclosure is to provide a pharmaceutical composition, characterized in that the pharmaceutical composition comprises the pharmaceutical solution of the present disclosure, at least one anti-tumor drug, and optionally one or more pharmaceutically acceptable excipients.

Another aspect of the present disclosure is to provide use of the pharmaceutical solution, the pharmaceutical composition, or the medicament for combinational administration according to the present disclosure in the manufacture of an anti-tumor agent.

Another aspect of the present disclosure is to provide a method for preventing or treating tumors, comprising administering a therapeutically effective amount of the pharmaceutical solution, the pharmaceutical composition, or the medicament for combinational administration according to the present disclosure, to a mammal having a tumor.

Another aspect of the present disclosure is to provide a method for preventing or treating tumors, characterized in that the medicament for combinational administration comprises deuterium oxide and at least one anti-tumor drug, wherein the deuterium oxide and the anti-tumor drug may be administered separately or concomitantly.

Another aspect of the present disclosure is to provide a method for preventing or treating tumors, wherein the pharmaceutical solution, the medicament for combinational administration, and the pharmaceutical composition are a solution for lavage and perfusion, a solution for injection, a suspension, an emulsion, or an embolization.

Another aspect of the present disclosure is to provide a method for preventing or treating tumors, comprising administering a therapeutically effective amount of the pharmaceutical solution, the pharmaceutical composition, or the medicament for combinational administration according to the present disclosure to a mammal having a tumor by various administration routes, excluding oral administration, including intravenous injection or instillation, intra-arterial injection, topical perfusion and lavage, topical hyperthermic perfusion and lavage, trascatheter embolization, topical intratumoral and peritumoral administration.

Another aspect of the present disclosure is to provide a method for preventing or treating malignant tumors, wherein administration by perfusion and lavage is performed by perfusing and lavaging topical sites of the mammal having a tumor, such as thoracic cavity, peritoneal cavity, pelvic cavity, bladder cavity, buccal cavity, nasal cavity, enteric cavity, uterine cavity, articular cavity, and skin, with a solution for perfusion and lavage.

Another aspect of the present disclosure is to provide a method for preventing or treating malignant tumors, wherein in administration by hyperthermic perfusion and lavage, the temperature of the solution for perfusion and lavage is 40° C. to 48° C., preferably 42° C. to 44.5° C., and more preferably 42° C.

Another aspect of the present disclosure is to provide a method for preventing or treating malignant tumors, wherein in administration by perfusion and lavage or by hyperthermic perfusion and lavage, the dose of the solution for perfusion and lavage are 5 to 6,000 ml/administration to the mammal having a tumor.

Another aspect of the present disclosure is to provide a method for preventing or treating malignant tumors, wherein in administration by intravenous injection, intra-arterial injection, intrathecal injection, or intratumoral and peritumoral injection, the dose of the solution for injection is 1 ml/kg to 20 ml/kg to the mammal having a tumor.

In the method according to the present disclosure, the mammal is selected from a rodent and a human.

Another aspect of the present disclosure is to provide use of deuterium oxide in the manufacture of a pharmaceutical solution.

Figure 1:
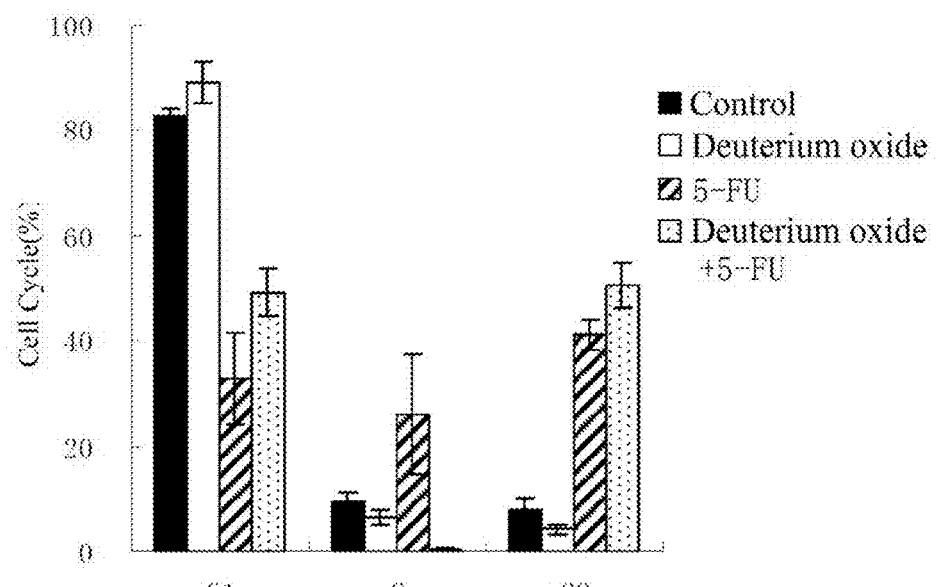
FIG. 1. Effect of deuterium oxide on the cell cycle of human colon cancer HCT-166 cells, as measured by the FCM method.
Figure 2:
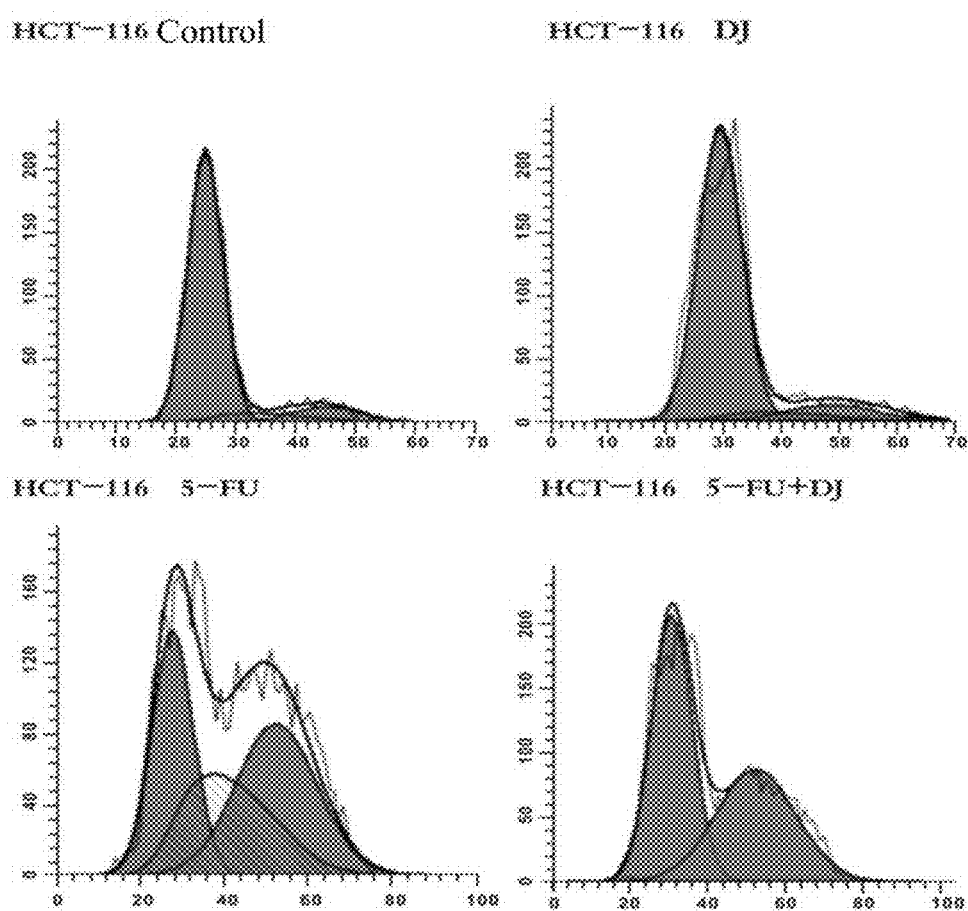
FIG. 2. Effect of deuterium oxide on the cell cycle of human lung cancer A549 cells.
Figure 3:
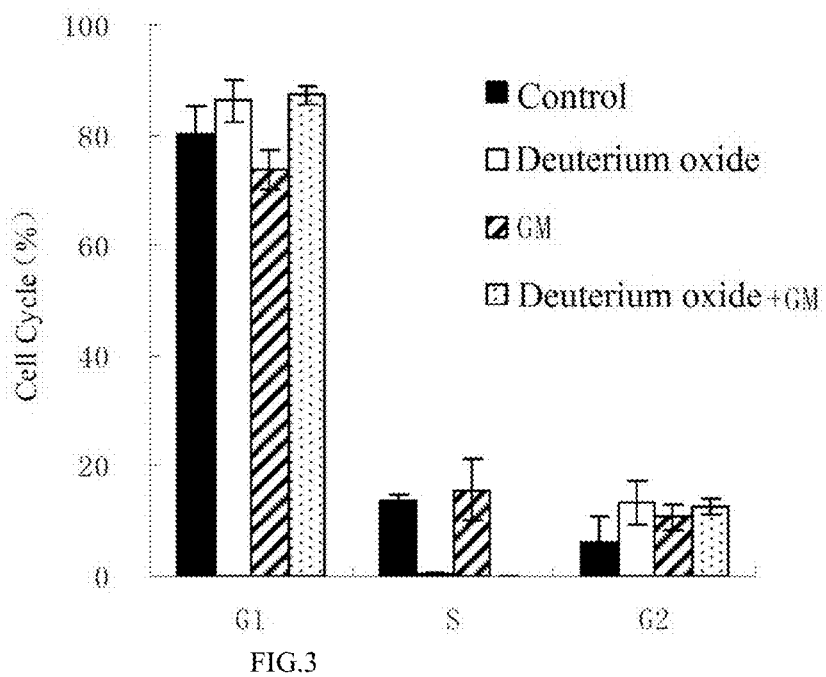
FIG. 3. Effect of deuterium oxide on the cell cycle of human lung cancer A549 cells, as measured by the FCM method.
Figure 4:
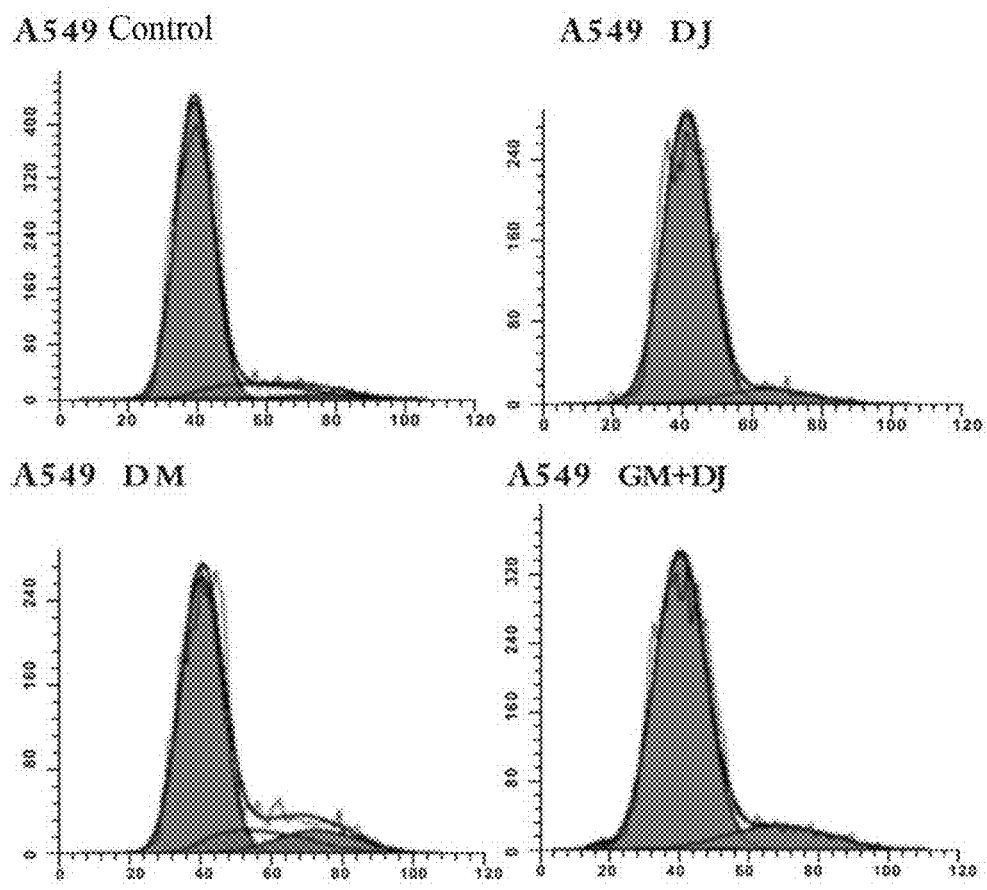
FIG. 4. Effect of the glucose deuterium oxide solution in combination with 5-FU on the tumor size of xenograft tumors from human colon cancer HCT-166 cells in nude mice.

In the figures, both DJ and HW refer to deuterium oxide.

DETAILED DESCRIPTION

The present application relates to the following embodiments.

Embodiment 1. A pharmaceutical solution, characterized by using deuterium oxide as a solvent.

Embodiment 2. The pharmaceutical solution according to Embodiment 1, characterized in that, the pharmaceutical solution comprises sodium chloride and deuterium oxide, being a sodium chloride deuterium oxide solution containing 0.1 g to 5 g sodium chloride, preferably 0.5 g to 2.5 g sodium chloride per 100 ml solution.

Embodiment 3. The pharmaceutical solution according to Embodiment 1, characterized in that, the pharmaceutical solution comprises sodium chloride and deuterium oxide, being a sodium chloride deuterium oxide solution containing 0.9 g sodium chloride per 100 ml solution, which is prepared with deuterium oxide and sodium chloride and has a pH of 4.5 to 7.0.

Embodiment 4. The pharmaceutical solution according to Embodiment 1, characterized in that, the pharmaceutical solution comprises glucose and deuterium oxide, being a glucose deuterium oxide solution containing 0.1 g to 50 g glucose, preferably 5 to 10 g, most preferably 5 g glucose per 100 ml pharmaceutical solution, which is prepared with deuterium oxide and glucose and has a pH of 3.2 to 6.5.

Embodiment 5. The pharmaceutical solution according to Embodiment 1, characterized in that, the pharmaceutical solution comprises glucose and sodium chloride and deuterium oxide, being a glucose sodium deuterium oxide solution containing 0.9 g sodium chloride and 5 g glucose per 100 ml pharmaceutical solution, which is prepared with deuterium oxide, sodium chloride and glucose and has a pH of 3.5 to 5.5.

Embodiment 6. The pharmaceutical solution according to Embodiment 1, characterized in that, the pharmaceutical solution comprises sodium bicarbonate and deuterium oxide, being a sodium bicarbonate deuterium oxide solution containing 1 to 10 g, preferably 5 to 10 g, most preferably 5 g sodium bicarbonate per 100 ml pharmaceutical solution, which is prepared with deuterium oxide and sodium bicarbonate and has a pH of 7.5 to 8.5.

Embodiment 7. The pharmaceutical solution according to Embodiment 1, characterized in that, the pharmaceutical solution is a Ringer's deuterium oxide solution containing 0.85 g sodium chloride, 0.012 g potassium chloride and 0.024 g calcium chloride ($CaCl_2.2H_2O$) per 100 ml pharmaceutical solution, which is prepared with deuterium oxide, sodium chloride, potassium chloride and calcium chloride and has a pH of 4.5 to 7.5.

Embodiment 8. The pharmaceutical solution according to Embodiment 1, characterized in that, the pharmaceutical solution comprises sodium hyaluronate and deuterium oxide, being a sodium hyaluronate deuterium oxide solution containing 0.04 to 3 g, preferably 0.08 to 1.4 g sodium hyaluronate, most preferably being a sodium hyaluronate deuterium oxide solution containing 0.08 or 1.0 g sodium hyaluronate, 0.9 g sodium chloride, 0.142 g disodium hydrogen phosphate and 0.027 g sodium dihydrogen phosphate per 100 ml pharmaceutical solution and having a pH adjusted to 6.5 to 7.5.

Embodiment 9. The pharmaceutical solution according to Embodiment 1, characterized in that, the pharmaceutical solution comprises hydroxyethyl starch and deuterium oxide, being a hydroxyethyl starch deuterium oxide solution containing 3 to 8 g hydroxyethyl starch, most preferably being a solution of hydroxyethyl starch and sodium chloride in deuterium oxide containing 6 g hydroxyethyl starch and 0.9 g sodium chloride per 100 ml pharmaceutical solution and having a pH adjusted to 6.0 to 7.0.

Embodiment 10. The pharmaceutical solution according to Embodiment 1, characterized in that, the pharmaceutical solution comprises hydroxypropyl-β-cyclodextrin (HP-β-CD) and deuterium oxide, being a HP-β-CD deuterium oxide solution containing 0.4 to 10 g HP-β-CD, most preferably being a HP-β-CD sodium chloride deuterium oxide solution containing 10 g HP-β-CD and 0.9 g sodium chloride per 100 ml pharmaceutical solution and having a pH adjusted to 5.0 to 7.0.

Embodiment 11. The pharmaceutical solution according to Embodiment 1, characterized in that, the pharmaceutical solution comprises human albumin and deuterium oxide, being a human albumin deuterium oxide solution containing 5 to 25 g human albumin, most preferably being a human albumin deuterium oxide solution containing 5 or 20 g human albumin per 100 ml pharmaceutical solution and having a pH adjusted to 5.0 to 7.0.

Embodiment 12. The pharmaceutical solution according to Embodiment 1, characterized in that, the pharmaceutical solution comprises polyethylene glycol (MW:300) and deuterium oxide, being a polyethylene glycol deuterium oxide solution containing 1 to 50 g polyethylene glycol, most preferably being a polyethylene glycol deuterium oxide solution containing 10 g polyethylene glycol per 100 ml pharmaceutical solution and having a pH adjusted to 5.0 to 7.0.

Embodiment 13. The pharmaceutical solution according to Embodiment 1, characterized in that, the pharmaceutical solution comprises amino acid, which L-proline ($C_5H_9NO_2$) 1.00 g, L-serine ($C_3H_7NO_3$) 1.00 g, L-alanine ($C_3H_7NO_2$) 2.00 g, L-isoleucine ($C_6H_{13}NO_2$) 3.52 g, L-leucine ($C_6H_{13}NO_2$) 4.90 g, L-aspartate ($C_4H_7NO_4$) 2.50 g, L-tyrosine ($C_9H_{11}NO_3$) 0.25 g, L-glutamate ($C_5H_9NO_4$) 0.75 g L-phenylalanine ($C_9H_{11}NO_2$) 5.33 g, L-Arginine ($C_6H_{14}N_4O_2.HCl$) 5.00 g, L-Lysine ($C_6H_{14}N_2O_2.HCl$) 4.30 g, L-valine ($C_5H_{11}NO_2$) 3.60 g, L-threonine ($C_4H_9NO_3$) 2.50 g, L-histidine ($C_6H_9N_3O_2.HCl.H_2O$) 2.50 g, L-Tryptophan ($C_{11}H_{12}N_2O_2$) 0.90 g, L-methionine ($C_{15}H_{11}NO_2S$) 2.25 g, L-Cystine ($C_6H_{12}N_2O_4S_2$) 0.10 g, glycine ($C_2H_5NO_2$) 7.60 g, sorbitol ($C_6H_{14}O_6$) 50.00 g, Sodium bisulfite ($NaHSO_3$) 0.5 g and deuterium oxide, being a amino acid deuterium oxide solution, having a pH adjusted to 5.0 to 7.0.

Embodiment 14. The pharmaceutical solution according to Embodiments 1 to 13, characterized in that, the pharmaceutical solution is a solution for lavage and perfusion, a solution for injection, a suspension, an emulsion, or a solution for embolization.

Embodiment 15. An anti-tumor medicament for combinational administration, characterized in that the medicament comprises the pharmaceutical solution according to any one of Embodiments 1 to 13, at least one anti-tumor drug, and optionally one or more pharmaceutically acceptable excipients.

Embodiment 16. The medicament for combinational administration according to Embodiment 15, wherein the anti-tumor drug is selected from anti-tumor cytotoxic drugs and monoclonal antibody anti-tumor drugs.

Embodiment 17. The medicament for combinational administration according to Embodiment 16, wherein the anti-tumor cytotoxic drugs include antimetabolites, phytogenic anti-tumor drugs, tumor antibiotics, alkylating agents, monoclonal antibodies, and platinum preparations.

Embodiment 18. The medicament for combinational administration according to Embodiment 17, wherein the antimetabolites include 5-fluorouracil, gemcitabine, floxuridine, pemetrexed, raltitrexed, fludarabine, cytarabine; the tumor antibiotics include mitomycin, epirubicin, peplomycin, daunorubicin, adriamycin, pirarubicin, aclarubicin; the platinum preparations include cisplatin, oxaliplatin, carboplatin, nedaplatin; the phytogenic anti-tumor drugs include paclitaxel, paclitaxel liposomes, paclitaxel albumin, docetaxel, etoposide, hydroxycamptothecin; the alkylating agents include Nivolumab, carmustine, nimustine, fotemustine, estramustine, cyclophosphamide, myleran.

Embodiment 19. The medicament for combinational administration according to Embodiment 17 wherein the monoclonal antibody anti-tumor drugs include bevacizumab, cetwimab, trastuzumab, panitumumab, nimotuzumab, recombinant human endostatin.

Embodiment 20. An anti-tumor pharmaceutical composition, characterized in that the pharmaceutical composition comprises the pharmaceutical solution according to any one of Embodiments 1 to 13, at least one anti-tumor drug, and optionally one or more pharmaceutically acceptable excipients.

Embodiment 21. The pharmaceutical composition according to Embodiment 17, wherein the anti-tumor drug is selected from anti-tumor cytotoxic drugs and monoclonal antibody anti-tumor drugs.

Embodiment 22. The pharmaceutical composition according to Embodiment 18, wherein the anti-tumor cytotoxic drugs include antimetabolites, phytogenic anti-tumor drugs, tumor antibiotics, alkylating agents, monoclonal antibodies, and platinum preparations.

Embodiment 23. The pharmaceutical composition according to Embodiment 16, 17, wherein the antimetabolites include 5-fluorouracil, gemcitabine, floxuridine, pemetrexed, raltitrexed, fludarabine, cytarabine; the tumor antibiotics include mitomycin, epirubicin, peplomycin, daunorubicin, adriamycin, pirarubicin, aclarubicin; the platinum preparations include cisplatin, oxaliplatin, carboplatin, nedaplatin; the phytogenic anti-tumor drugs include paclitaxel, paclitaxel liposomes, paclitaxel albumin, docetaxel, etoposide, hydroxycamptothecin; the alkylating agents include Nivolumab, carmustine, nimustine, fotemustine, estramustine, cyclophosphamide, myleran.

Embodiment 24. The pharmaceutical composition according to Embodiment 19, wherein the monoclonal antibody anti-tumor drugs include bevacizumab, cetuximab, trastuzumab, panitumumab, nimotuzumab, recombinant human endostatin.

Embodiment 25. Use of the pharmaceutical solution according to any one of Embodiments 1 to 13, the medicament for combinational administration according to any one of Embodiments 14 to 19, or the pharmaceutical composition according to any one of Embodiments 14 to 23, in the manufacture of an anti-tumor agent.

Embodiment 26. The pharmaceutical solution according to any one of Embodiments 1 to 13, the medicament for combinational administration according to any one of Embodiments 14 to 19, or the pharmaceutical composition according to any one of Embodiments 20 to 21, for use in treatment or prevention of tumors.

Embodiment 27. A method for treating or preventing tumors, comprising administering a therapeutically effective amount of the pharmaceutical solution, the pharmaceutical composition, or the medicament for combinational administration according to the present disclosure to a mammal having a tumor by various administration routes, excluding oral administration, including intravenous injection or instillation, intra-arterial injection, topical perfusion and lavage, topical hyperthermic perfusion and lavage, transcatheter embolization, topical intrathecal injection, and intratumoral and peritumoral injection.

Embodiment 28. In Embodiment 26 or 27, in the administration by hyperthermic perfusion and lavage, the temperature of the solution for lavage and perfusion is 40° C. to 48±1° C., preferably 42° C. to 44.5±1° C., and more preferably 42±1° C.

Embodiment 29. In Embodiment 28, the administration by topical perfusion and lavage or by topical hyperthermic perfusion and lavage is performed by perfusing and lavaging topical sites, such as thoracic cavity, peritoneal cavity, pelvic cavity, bladder cavity, buccal cavity, nasal cavity, enteric cavity, uterine cavity, articular cavity, and skin, of the mammal with a solution for lavage and perfusion in a dose of 5 to 6,000 ml/administration.

Embodiment 30. In Embodiment 29, in the administration by intravenous injection, intra-arterial injection, intrathecal injection, or intratumoral and peritumoral injection, the dose of the solution for injection is 1 ml/kg to 20 m/kg.

Embodiment 31. A method for treating or preventing tumors, comprising administering a therapeutically effective amount of the pharmaceutical solution according to any one of Embodiments 1 to 13, the medicament for combinational administration according to any one of Embodiments 14 to 19, or the pharmaceutical composition according to any one of Embodiments 20 to 24 to a mammal having a tumor.

Embodiment 32. Use of deuterium oxide in the manufacture of the pharmaceutical solution according to any one of Embodiments 1 to 13.

In the pharmaceutical solution or pharmaceutical composition according to the present disclosure, every 100 ml of the pharmaceutical solution or pharmaceutical composition contains 1 to 99.9 g deuterium oxide, preferably 9 to 99.9 g deuterium oxide, more preferably 20 to 99.9 g deuterium oxide, even more preferably 30 to 99.9 g deuterium oxide, even more preferably 40 to 99.9 g deuterium oxide, even more preferably 50 to 99.9 g deuterium oxide, even more preferably 60 to 99.9 g deuterium oxide, even more preferably 70 to 99.9 g deuterium oxide, even more preferably 80 to 99.9 g deuterium oxide, even more preferably 90 to 99.9 g deuterium oxide, even more preferably 95 to 99.9 g deuterium oxide, and most preferably 99.6 to 99.9 g deuterium oxide.

Deuterium oxide according to the present disclosure is produced by deuterium oxide plants, and is commercially available. In the deuterium oxide the isotope abundance of deuterium is 1 to 99.9%, preferably 30 to 99.9%, more preferably 50 to 99.9%, more preferably 90 to 99.9%, and most preferably 99.6 to 99.9%. For example the deuterium oxide provided by Cambridge Isotope Laboratories, Inc. USA, may be used, which has an isotope abundance of deuterium of 90 to 99.9%, preferably 99.6 to 99.90 (D 99.6-99.9%).

The pharmaceutically excipients may be water, sodium chloride, potassium chloride, calcium chloride, magnesium chloride, sodium lactate, sodium acetate, sodium citrate, sodium bicarbonate, potassium dihydrogen phosphate, disodium hydrogenphosphate, sodium bicarbonate, glucose, fructose, albumin, liposomes, hyaluronic acid, and/or polyethylene glycol.

The anti-tumor drug is selected from anti-tumor cytotoxic drugs and monoclonal antibody anti-tumor drugs.

The anti-tumor cytotoxic drugs include antimetabolites, phytogenic anti-tumor drugs, tumor antibiotics, alkylating agents, monoclonal antibodies, and platinum preparations. The antimetabolites include 5-fluorouracil, gemcitabine, floxuridine, pemetrexed, raltitrexed, fludarabine, cytarabine; preferably 5-fluorouracil, gemcitabine, and pemetrexed. The tumor antibiotics include mitomycin, epirubicin, peplomycin, daunorubicin, adriamycin, pirarubicin, aclarubicin; preferably mitomycin and epirubicin. The platinum preparations include cisplatin, oxaliplatin, carboplatin, nedaplatin; preferably cisplatin and oxaliplatin. The phytogenic anti-tumor drugs include paclitaxel, paclitaxel liposomes, paclitaxel albumin, docetaxel, etoposide, hydroxycamptothecin; preferably paclitaxel, paclitaxel liposomes, paclitaxel albumin, and docetaxel. The alkylating agents include Nivolumab, carmustine, nimustine, fotemustine, estramustine, cyclophosphamide, myleran; preferably Nivolumab and carmustine.

The monoclonal antibody anti-tumor drugs include bevacizumab, cetuximab, trastuzumab, panitumumab, nimotuzumab, recombinant human endostatin; preferably bevacizumab and recombinant human endostatin.

The pharmaceutical solution according to the present disclosure is prepared by standard methods for preparing solution in the field of pharmaceutics, and satisfies relevant standards in *Chinese Pharmacopoeia, United States Pharmacopoeia*, and *European Pharmacopoeia*.

When the pharmaceutical solution according to the present disclosure is combined with anti-tumor drugs, the dissolution or dilution ratios of anti-tumor drugs in the pharmaceutical solution prescribed in *Chinese Pharmacopoeia, United States Pharmacopoeia*, and *European Pharmacopoeia* are used.

The medicament for combinational administration according to the present disclosure refers to combined administration of one pharmaceutical solution according to the present disclosure and one or more anti-tumor drugs.

The pharmaceutical composition according to the present disclosure is a composite formulation prepared from a pharmaceutical solution and one or more anti-tumor drugs.

The components in the pharmaceutical solution, the pharmaceutical composition, or the medicament for combinational administration according to the present disclosure may be administered separately or concomitantly.

The pharmaceutical solution, the pharmaceutical composition, or the medicament for combinational administration according to the present disclosure is various preparations such as a solution for perfusion and lavage, a solution for injection, a suspension, an emulsion, or a solution for embolization.

The tumor according to the present disclosure is selected from lung cancer, colorectal cancer, primary liver cancer, esophageal cancer, gastric cancer and cardiac cancer, pancreatic cancer, renal cell carcinoma, bladder cancer, prostate cancer, head and neck cancer, nasopharyngeal cancer, cervical cancer, ovarian cancer, breast cancer, brain tumor, bone and joint sarcoma, thyroid cancer, skin cancer, malignant melanoma, malignant lymphoma, leukemia, and complications and recurrence of various malignant tumors, such as thoracic, peritoneal and/or pelvic cavity metastasis and implantation of tumor cells, and malignant effusion in thoracic, peritoneal and/or pelvic cavity.

In the method according to the present disclosure, the mammal is selected from a rodent and a human.

The word "comprise" or "comprising" used herein encompasses both the case where the substance(s) or component(s) referred to is exclusively included, and the case where other substance(s) or component(s) that does not interfere with the accomplishment of the intended objective is also included in addition to the substance or component referred to.

Unless otherwise specified, all values used herein to indicate the amount of a substance should be construed as being modified by the term "approximately".

The present disclosure will be further described in the below examples. It is to be understood that the scope of the present disclosure is not limited to the examples.

All cell lines used in the examples of the present disclosure are commercially available.

Example 1

0.9 g sodium chloride was weighed out, to which 99 g deuterium oxide (D, 99.6-99.8%, from Cambridge Isotope Laboratories, Inc., USA, the same below) was added to dissolve the sodium chloride under stirring. Drops of a sodium hydroxide solution were added to adjust the solution pH to 7.0, and then deuterium oxide was added to a final volume of 100 ml. The solution was sterilized by filtration through a 0.2 μm millipore filter and sealed in a container, to obtain a sodium chloride deuterium oxide solution containing 0.9 g sodium chloride per 100 ml pharmaceutical solution according to the present disclosure.

Example 2

5 g glucose was weighed out, to which 99 g deuterium oxide was added to dissolve the glucose under stirring. Drops of a hydrochloric acid solution were added to adjust the pH to 5.5, and then deuterium oxide was added to a final volume of 100 ml. The solution was sterilized by filtration through a 0.2 μm millipore filter and sealed in a container, to obtain a 5% glucose deuterium oxide solution containing 5 g glucose per 100 ml pharmaceutical solution according to the present disclosure.

Example 3

10 g glucose was weighed out, to which 99 g deuterium oxide was added to dissolve the glucose under stirring. Drops of a hydrochloric acid solution were added to adjust the pH to 5.5, and then deuterium oxide was added to a final volume of 100 ml. The solution was sterilized by filtration through a 0.2 μm millipore filter and sealed in a container, to obtain a 10% glucose deuterium oxide solution containing 10 g glucose per 100 ml pharmaceutical solution according to the present disclosure.

Example 4

0.9 g sodium chloride and 5 g glucose were separately weighed out, to which 99 g deuterium oxide was added to dissolve them under stirring. Drops of a hydrochloric acid solution were added to adjust the pH to 5.0, and then deuterium oxide was added to a final volume of 100 ml. The solution was sterilized by filtration through a 0.2 μm millipore filter, sealed in a container, to obtain a glucose sodium chloride deuterium oxide solution containing 0.9 g sodium chloride and 5 g glucose per 100 ml pharmaceutical solution according to the present disclosure.

Example 5

5 g sodium bicarbonate was separately weighed out, to which 99 g deuterium oxide was added to dissolve it under stirring. Drops of a hydrochloric acid solution were added to adjust the pH to 8.0, and then deuterium oxide was added to a final volume of 100 ml. The solution was sterilized by filtration through a 0.2 μm millipore filter and sealed in a container, to obtain a 5% sodium bicarbonate deuterium oxide solution containing 5 g sodium bicarbonate per 100 ml pharmaceutical solution according to the present disclosure.

Example 6

0.85 g sodium chloride, 0.03 g potassium chloride and 0.033 g calcium chloride ($CaCl_2 \cdot 2H_2O$) were separately weighed out, to which 99 g deuterium oxide was added to dissolve them under stirring. Drops of a sodium hydroxide solution were added to adjust the pH to 7.0, and then deuterium oxide was added to a final volume of 100 ml. The solution was sterilized by filtration through a 0.2 μm millipore filter, and sealed in a container, to obtain a Ringer's deuterium oxide solution according to the present disclosure.

Example 7

0.8 g sodium chloride, 0.04 g potassium chloride, 0.1 g glucose, 0.006 g potassium dihydrogen phosphate, 0.00475 g disodium hydrogen phosphate, and 0.22 g sodium bicarbonate were separately weighed out, to which 99 g deuterium oxide was added to dissolve them under stirring. Drops of a sodium hydroxide solution were added to adjust the pH to 7.0, and then deuterium oxide was added to a final volume of 100 ml. The solution was sterilized by filtration through a 0.2 μm millipore filter, and sealed in a container, to obtain an Earle's balanced salt deuterium oxide solution according to the present disclosure.

Example 8

A method for preparing a warm (40° C. to 48° C.) 0.08% sodium hyaluronate deuterium oxide solution. Sodium hyaluronate, (HA, CAS: 9067-32-7, Formula: $(C_{14}H_{20}O_{11}N)_n$, Mw: $10^5$ to $10^7$). The solution comprising 0.08 g sodium hyaluronate, 0.8 g sodium chloride, 0.142 g disodium hydrogen phosphate ($Na_2HPO_4 \cdot 12H_2O$) and 0.027 g sodium dihydrogen phosphate ($NaH_2PO_4$) per 100 ml solution, and having a pH of 6.5 to 7.5. Detailed steps of the method: 0.8 g sodium chloride, 0.142 g disodium hydrogen phosphate ($Na_2HPO_4 \cdot 12H_2O$) and 0.027 g sodium dihydrogen phosphate ($NaH_2PO_4$) was separately weighed out, dissolved in 80 g deuterium oxide to make a solution, which was boiled and sterilized, then 0.08 g sterile sodium hyaluronate was added and dissolved, the volume was metered to 100 ml with deuterium oxide, the pH was adjusted to 6.0 to 7.0, and the solution was sterilized by 0.2 μm millipore filtration to obtain 0.08% sterile sodium hyaluronate deuterium oxide solution, which was filled into a container. For topical perfusion and lavage, the solution was warmed to a temperature of 40° C. to 48° C. in a hyperthermic perfusion and lavage apparatus, mixed with various anti-tumor drugs, and administered by topical perfusion and lavage.

Example 9

A method for preparing a 1.0% sodium hyaluronate deuterium oxide solution comprising 10 g sodium hyaluronate, 8 g sodium chloride, 1.42 g disodium hydrogen phosphate ($Na_2HPO_4.12H_2O$) and 0.27 g sodium dihydrogen phosphate ($NaH_2PO_4$) per 1000 ml solution, and having a pH of 6.5 to 7.5. Detailed steps of the method: 8 g sodium chloride, 1.42 g disodium hydrogen phosphate ($Na_2HPO_4.12H_2O$) and 0.27 g sodium dihydrogen phosphate ($NaH_2PO_4$) was separately weighed out, dissolved in 800 g deuterium oxide to make a solution, which was boiled and sterilized by filtration, then 10 g sterile sodium hyaluronate was added and dissolved, the volume was metered to 1000 ml with deuterium oxide, the pH was adjusted to 6.0 to 7.5, and the solution was sterilized by 0.2 µm millipore filtration to obtain a 1.0% sterile sodium hyaluronate deuterium oxide solution, which was filled into a container and was ready for use.

Example 10

A method for preparing a perfusion and lavage solution of 6% hydroxyethyl starch (200/0.5) deuterium oxide solution. Hydroxyethyl Starch (CAS: 9005-27-0, Mw 580.5. Formula $C_{22}H_{44}O_{17}$). There are 4 types of hydroxyethyl starches having different molecular weights: hydroxyethyl starch (20), hydroxyethyl starch (40), hydroxyethyl starch (130/0.4), and hydroxyethyl starch (200/0.5), all of which can be made into a perfusion and lavage solution of hydroxyethyl starch, and among which hydroxyethyl starch (200/0.5) is preferred. Detailed steps of the method: 60 g hydroxyethyl starch (200/0.5) was weighed out, dissolved in 500 g deuterium oxide to make a solution; 9 g sodium chloride was dissolved in another 500 g deuterium oxide, then the solution of hydroxyethyl starch (200/0.5) deuterium oxide and the solution of sodium chloride deuterium oxide were mixed in a ratio of 1:1, the volume was metered to 1000 ml with deuterium oxide, the pH was adjusted to 6.0 to 7.0, and the solution was sterilized by 0.2 µm millipore filtration and sealed in a container and was ready for use.

Example 11

A method for preparing a hydroxypropyl-β-cyclodextrin deuterium oxide solution. Hydroxypropyl-β-cyclodextrin (HP-β-CD, CAS: 128446-35-5. Mw: 1431-1806. Formula: $(C_{42}H_{70}O_{35})$-Hn+$(C_3H_7O_2)$n) comprising HP-β-CD as a solute and deuterium oxide as a solvent, wherein the concentration of HP-β-CD in the solution is 0.4 to 10 wt %, preferably 10 wt %. Detailed steps of the method: 10 g HP-β-CD was weighed out and dissolved in 100 g deuterium oxide under stirring. The solution contained 10 g HP-β-CD per 100 ml pharmaceutical solution, the pH was adjusted to 5.0 to 7.0, and the solution was sterilized by 0.2 µm millipore filtration and sealed in a container and was ready for use.

Example 12

A method for preparing a sulfobutylether-β-cyclodextrin-deuterium oxide solution. Sulfobutylether-β-cyclodextrin (SBE-β-CD. CAS: 25167-62-8) comprising SBE-β-CD as a solute and deuterium oxide as a solvent, wherein the concentration of SBE-β-CD in the solution is 3 to 30 wt %, preferably 10 wt %. Most preferably, the solution contained 10 g SBE-β-CD per 100 ml pharmaceutical solution. Detailed steps of the method: 10 g SBE-β-CD was weighed out and dissolved in 100 g deuterium oxide under stirring, the pH was adjusted to 5.0 to 7.0, and the solution was sterilized by 0.2 µm millipore filtration and sealed in a container and was ready for use.

Example 13

A method for preparing a human serum albumin freeze-dry powder deuterium oxide solution. Human serum albumin freeze-dry powder as a solute and deuterium oxide as a solvent, wherein the concentration of human serum albumin in the solution is 5-20%. Detailed steps of the method 5-20 g human serum albumin freeze-dry powder was weighed out and dissolved in 100 g deuterium oxide under stirring, the pH was adjusted to 5.0 to 7.0, and the solution was sterilized by 0.2 µm millipore filtration and sealed in a container and was ready for use.

Example 14

A method for preparing polyethylene glycol (MW:300) and deuterium oxide, being a polyethylene glycol deuterium oxide solution containing 1 to 50 g polyethylene glycol, most preferably being a polyethylene glycol deuterium oxide solution containing 10 g polyethylene glycol per 100 ml pharmaceutical solution and having a pH adjusted to 5.0 to 7.0.

Example 15

A method for preparing a compound amino acid deuterium oxide solution. Compound amino acid as a solute and deuterium oxide as a solvent. Detailed steps of the method: L-proline ($C_5H_9NO_2$) 1.00 g, L-serine ($C_3H_7NO_3$) 1.00 g, L-alanine ($C_3H_7NO_2$) 2.00 g, L-isoleucine ($C_4H_{13}NO_2$) 3.52 g, L-leucine ($C_6H_{13}NO_2$) 4.90 g, L-aspartate ($C_4H_7NO_4$) 2.50 g, L-tyrosine ($C_9H_{11}NO_3$) 0.25 g, L-glutamate ($C_3H_9NO_4$) 0.75 g, L-phenylalanine ($C_6H_{13}NO_2$) 5.33 g, L-arginine ($C_6H_{14}N_4O_2.HCl$) 5.00 g, L-lysine ($C_6H_{14}N_2O_2.HCl$) 4.30 g, L-valine ($C_5H_{11}NO_2$) 3.60 g, L-threonine ($C_4H_9NO_3$) 2.50 g, L-histidine ($C_6H_9N_3O_2.HCl.H_2O$) 2.50 g, L-tryptophan ($C_1H_{12}N_2O_2$) 0.90 g, L-methionine ($C_{15}H_{11}NO_2S$) 2.25 g, L-Cystine ($C_6H_{12}N_2O_4S_2$) 0.10 g, glycine ($C_2H_5NO_2$) 7.60 g, sorbitol ($C_6H_{14}O_6$) 50.00 g, Sodium bisulfite ($NaHSO_3$) 0.5 g were weighed out and dissolved in 1000 g deuterium oxide under stirring, the pH was adjusted to 5.0 to 7.0, and the solution was sterilized by 0.2 µm millipore filtration and sealed in a container and was ready for use.

Example 16

The method for warming the solution to a temperature of 40° C. to 48° C.: for a solution of or less than 50 ml, the container containing the solution to be used was placed on a small heater or in a water bath at the corresponding temperature for 10 to 20 min; for a solution more than 50 ml, the solution was heated to a temperature of 40° C. to 48° C. in a hyperthermic perfusion and lavage apparatus (BR-TRG-1 hyperthermic perfusion intraperitoneal treatment system, manufactured by Baorui Medical Technology Co., Ltd, Guangzhou, China) and was ready for use.

Example 17

Inhibition of growth of human colon cancer HCT-116 cells (a moderately drug resistant strain) by deuterium oxide in combination with 5-fluorouracil (5-FU), by the MTT (3-(4,5-dimethylthiazol-2-yl)-2,5-diphenyltetrazolium bromide) assay Cell line: all cell lines of various types shown in Table 1 were provided by NANJING KEYGEN BIOTECK CO., LTD and from ATCC, and were commercially available (the same below).

Test drugs: 5-fluorouracil (5-FU), and the sodium chloride deuterium oxide solution, prepared in Example 1.

Method: 5-fluorouracil was diluted with the sodium chloride deuterium oxide solution according to the concentrations shown in Table 1 and added to a cell culture plate; the in vitro inhibition of tumor cell growth was measured by the MTT assay.

Method:
1. A bottle of cells that had been cultured for 3 to 4 days and were in the exponential phase was taken, a suitable amount of 0.25% Trypsin-EDTA solution was added thereto to detach the cells from the wall, and the cells were suspended in 10 ml RPMI 1640 medium containing 10/FBS.
2. The cells were counted on a hemocytometer, and generally viable cells should be not less than 97%.
3. The cell suspension was diluted with a complete medium to prepare a suspension containing $1 \times 10^4$ cells/ml.
4. To each well of a 12-well culture plate, 300 µl cell suspension was added. The addition of cells should be finished within 4 hours. The plate was placed in an incubator at 37° C. and 5% $CO_2$ for 24 hours.
5. Powdery RPMI Medium 1640 (Gibco, USA, Cat #: 31800-022) was dissolved in deuterium oxide (provided by Cambridge Isotope Laboratories, Inc. (US)) to prepare a cell culture medium (unless particularly specified, all culture media used in the Examples hereinafter were prepared from powdery RPMI Medium 1640 and deuterium oxide) at a concentration shown in Table 1, which was added into the cell culture plate.
6. The cell culture plate was incubated for 3 days in an incubator at 37° C., 5% $CO_2$ and 100% humidity.
7. A solution of 1 mg/ml MTT was prepared in a serum-free RPMI1640 medium, added to the plate at 200 W/well, and incubated at 37° C. for 4 hours, to allow MTT to be reduced to formazan.
8. The supernatant was removed by pipetting, 200 µl DMSO was added to dissolve formazan, and the solution was well mixed on a platform shaker.
9. Absorbance of each well was measured on an ELISA reader with a detection wavelength of 570 nm and a reference wavelength of 450 nm.
10. The assay was repeated one more time.

Calculation of results: Inhibition of growth of tumor cells by deuterium oxide was calculated using tumor cells treated with sodium chloride physiological solution as a control group. Inhibition of cell growth was plotted against amounts of deuterium oxide to obtain a dose response curve, from which the half maximal inhibitory concentration ($IC_{50}$) of deuterium oxide was derived.

Inhibition of tumor cell growth (%)=(1−OD test/OD control)×100%

The assay was repeated one more time.

Result: it was found that 5-FU showed a certain inhibitory effect on growth of human colon cancer HCT-116 cells (a moderately drug resistant strain), and can significantly enhance the anti-tumor efficacy when combined with deuterium oxide, as shown in Table 1.

TABLE 1

Inhibition of growth of human colon cancer HCT-116 cells (a moderately drug resistant strain) by deuterium oxide in combination with 5-FU

| 5-FU Final conc. (µg/ml) | Inhibition of cell growth (%) (5-FU alone) | Inhibition of cell growth (%) [5-FU + 10% Deuterium oxide(v/v)] |
|---|---|---|
| 12.5 | 35.32 | 80.51 |
| 6.25 | 26.52 | 67.15 |
| 3.13 | 18.58 | 62.24 |
| 1.56 | 11.04 | 51.15 |
| 0.78 | 9.82 | 45.36 |
| 0.39 | 6.98 | 32.94 |
| 0.20 | 3.24 | 28.82 |
| 0.10 | 2.30 | 16.45 |
| 0.05 | 2.55 | 11.14 |
| 0.02 | 2.18 | 10.76 |

The results demonstrate that the combination of deuterium oxide and 5-FU enhances the inhibitory effect on growth of drug-resistant tumor cells (a moderately drug resistant strain); and especially at a low concentration of 5-FU, deuterium oxide shows a more significant efficacy-enhancing effect Therefore, deuterium oxide has a sensitizing effect against drug resistance.

Example 18

Effect of Deuterium Oxide on the Cell Cycle of Human Lung Cancer A549 Cells and Human Colon Cancer HCT-116 Cells Materials Human lung cancer A549 cells and human colon cancer HCT-116 cells were provided by NANJING KEYGEN BIOTECH. CO., LTD., and cultured in an incubator at 37° C., 5% $CO_2$ and saturated humidity.

A KGA511 Cell cycle assay kit was provided by NANJING KEYGEN BIOTECH. CO., LTD.

The flow cytometer was FACS Calibur provided by Becton-Dickinson, US.

Test drugs: gemcitabine (GEM), 5-fluorouracil (5-FU), and the sodium chloride deuterium oxide solution, prepared in Example 1.

Method:
Cell Culturing
1. Cell Resuscitation
1.1. Warm water at 37° C. to 40° C. was prepared, a cryogenic vial of cells was taken out of liquid nitrogen and immediately put into the 37° C.-40° C. warm water, followed by vigorous shaking until the cryogenic liquid was completely thawed;
1.2. The suspension of cryogenic cells was transferred to a centrifugal tube, 5 ml culture medium was added thereto, and the cells were well mixed in the medium by gentle pipetting;
1.3. The cell suspension was centrifuged at 800 to 1,000 rpm for 5 min, and the supernatant was discarded;
1.4. A complete culture medium was added to the cell pellet which was well mixed by gentle pipetting, the cell suspension was transferred to a culture flask, and the cells were cultured by supplementing culture medium.
2. Cell Subculturing
2.1. The original culture medium was removed by pipetting when the cell coverage reached 80% to 90% in the culture bottle;
2.2. A suitable amount of trypsin (0.25%) was added to digest for 1 to 2 min;
2.3. When all the cells became round, an equal volume of culture medium containing serum was added to cease the digestion;
2.4. The cells were blown by pipetting to suspend, then drawn into a 15 ml centrifugal tube, and centrifuged at 1000 rpm for 5 min;
2.5. The supernatant was discarded, and the cells were re-suspended in 1 to 2 ml culture medium and transferred to a culture bottle for further culturing.
Detection of Cell Cycle by PI Single Staining
1. Cells growing in the exponential phase were digested and inoculated to a 6-well plate; on the next day, after the cells attached to the wall, cell culture media containing corresponding test drugs were added according to different groups, and a negative control group was also set;
2. After treatment with test drugs for 72 hours, cells were digested with 0.25% pancreatin (EDTA-free) and collected;
3. The cells were washed with PBS once (centrifuged at 2,000 rpm for 5 min), and 5×10 cells were collected;
4. The prepared suspension of individual cells was fixed with 70% (v/v) ethanol for 2 hours (or overnight), and stored at 4° C.; before staining, the fixing solution was washed away with PBS (if necessary, the cell suspension was filtered once through a 200-mesh screen);
5. 100 µl RNase A was added, and the cells were water-bathed at 37° C. for 30 min;
6. 400 µl PI was added and well mixed for staining, and the cells were kept at 4° C. in darkness for 30 min;
7. In a detection apparatus, red fluorescence with an excitation wavelength of 488 nm was recorded.
Results

TABLE 2

Effect of deuterium oxide on the cell cycle of human colon cancer HCT-116 cells (%, $\bar{X} \pm SD$, n = 6)

| | G1 Phase | S Phase | G2 Phase |
|---|---|---|---|
| Control (sodium chloride physiological solution) | 82.53 ± 1.76 | 9.40 ± 1.83 | 8.06 ± 1.89 |
| Deuterium oxide (30%, v/v) | 89.19 ± 3.81 | 6.61 ± 1.41 | 4.21 ± 0.95 |
| 5-FU (12.5 ug/ml in sodium chloride physiological solution) | 32.69 ± 8.66 | 26.07 ± 11.32 | 41.24 ± 2.97 |
| Deuterium oxide(30%, v/v) + 5-FU(12.5 ug/ml) | 49.16 ± 4.47 | 0.30 ± 0.26 | 50.53 ± 4.26 |

TABLE 3

Effect of deuterium oxide on the cell cycle of human lung cancer A549 cells (%, $\bar{x} \pm SD$, n = 6)

| | G1 Phase | S Phase | G2 Phase |
|---|---|---|---|
| Control (sodium chloride physiological solution) | 80.29 ± 5.02 | 13.50 ± 1.33 | 6.21 ± 4.52 |
| Deuterium oxide (30%, v/v) | 86.23 ± 3.69 | 0.31 ± 0.28 | 13.47 ± 3.94 |
| GM (250 nM in sodium chloride physiological solution) | 73.73 ± 3.73 | 15.55 ± 5.51 | 10.71 ± 2.39 |
| Deuterium oxide (30%, v/v) + GM(250 nM) | 87.32 ± 1.60 | 0.08 ± 0.01 | 12.6 ± 1.46 |

5-FU and gemcitabine are cytotoxic metabolite antitumor drugs, and mainly act on tumor cells in the DNA synthesis phase, i.e. the S phase. It can be seen in the results of Tables 2 and 3 and FIGS. 1-4 that deuterium oxide impeded tumor cells entering the G2 phase from the S phase; when deuterium oxide was combined with 5-FU and gemcitabine, 5-FU and gemcitabine kill the S-phase tumor cells more effectively, resulting in significant reduction in the S-phase tumor cells, and exerting a synergistic effect.

Example 19

Studying 1: Efficacy of intraperitoneal. perfusion with deuterium oxide in combination with 5-fluorouracil on Ehrlich ascites tumor (EAC)-bearing mice.

Studying 2: Evaluate the effectiveness of different preparations and administration routes of deuterium oxide on nude mice beard human colon cancer HCT-116 cell.

Laboratory animal: 4 to 5 week-aged male ICR mice, provided by Shanghai SIPPR-BK Laboratory Animal Co. Ltd.

Cell lines: Ehrlich ascites tumor cells, human colon cancer HCT-116 cells were provided by NANJING KEYGEN BIOTECH. CO., LTD.

Test drugs: 5-fluorouracil (5-FU), and the sodium chloride deuterium oxide solution, prepared in Example 1.

Studying: 1 Experimental Method

1. Modeling: EAC ascitic fluid was taken and adjusted to $1 \times 10^7$ cells/ml, which was inoculated into the peritoneal cavity of mice at 0.1 ml/mouse.
2. Grouping and dosing: the animals were randomized 3 days after inoculation, and meanwhile drugs were given to mice in each group, following the dosing scheme shown in Table 4.

TABLE 4

Grouping and dosing scheme, NS means sodium chloride physiological solution (same below).

| Groups | Drugs, I.P. administration | Inoculation | Dosing | Data |
|---|---|---|---|---|
| Group 1 | NS. 0.4 ml/animal | Giving NS for 3 days first, then giving drug on day 3, followed by inoculation | Then giving 0.4 ml NS on each day until death of the animal | |
| Group 2 | 5-FU 20 mg/kg alone (in NS) | Giving 5-FU for 3 days first, then giving drug on day 3, followed by inoculation | Then giving 5-FU 20 mg/kg on each day for 7 successive days (10 days in total), then discontinuing the drug | Days that the animal had survived were recorded |
| Group 3 | 5-FU 30 mg/kg alone (in NS) | Giving 5-FU for 3 days first, then giving drug on day 3, followed by inoculation | Then giving 5-FU 30 mg/kg on each day for 7 successive days (10 days in total), then discontinuing the drug | Days that the animal had survived were recorded |
| Group 4 | Sodium chloride deuterium oxide solution, alone, 0.4 ml/animal | Giving Sodium chloride deuterium oxide solution for 3 days first, then giving drug on day 3, followed by inoculation | Then giving 0.4 ml Sodium chloride deuterium oxide solution on each day until death of animal, without drug discontinuance | Days that the animal had survived were recorded |

The above 4 groups and Group 5, Group 6, Group 7 below, seven groups in total:

| Groups | Drugs, I.P. administration | Inoculation | Dosing | Data |
|---|---|---|---|---|
| Group 5 | Sodium chloride deuterium oxide solution 0.1 ml/animal + 5-FU 20 mg/kg | Giving drug for 3 days first, then giving drug on day 3, followed by inoculation | Then giving drug on each day for 10 days in total, then discontinuing the drug | Days that the animal had survived were recorded |
| Group 6 | Sodium chloride deuterium oxide solution 0.2 ml/animal + 5-FU 20 mg/kg | Giving drug for 3 days first, then giving drug on day 3, followed by inoculation | Then giving drug on each day for 10 days in total, then discontinuing the drug | Days that the animal had survived were recorded |
| Group 7 | Sodium chloride deuterium oxide solution 0.4 ml/animal + 5-FU 20 mg/kg | Giving drug for 3 days first, then giving drug on day 3, followed by inoculation | Then giving drug on each day for 10 days in total, then discontinuing the drug | Days that the animal had survived were recorded |

For the 4 groups below, Sodium chloride deuterium oxide solution (0.6 ml/animal) was given 3 times by intraperitoneal lavage followed by intraperitoneal administration of drugs to corresponding groups

| Groups | Drugs, I.P. administration | Inoculation | Dosing | Data |
|---|---|---|---|---|
| Group 8 | NS 0.4 ml/animal | Giving NS for 3 days first, then giving drug on day 3, followed by inoculation | Then giving 0.4 ml NS on each day until death of the animal | Days that the animal had survived were recorded |
| Group 9 | Sodium chloride deuterium oxide solution 0.1 ml/animal + 5-FU, 20 mg/kg | Giving drug for 3 days first, then giving drug on day 3, followed by inoculation | Then giving drug on each day for 10 days in total, then discontinuing the drug | Days that the animal had survived were recorded |
| Group 10 | Sodium chloride deuterium oxide solution 0.2 ml/animal + 5-FU, 20 mg/kg | Giving drug for 3 days first, then giving drug on day 3, followed by inoculation | Then giving drug on each day for 10 days in total, then discontinuing the drug | Days that the animal had survived were recorded |

TABLE 4-continued

Grouping and dosing scheme, NS means sodium chloride physiological solution (same below).

| Groups | Drugs, I.P. administration | Inoculation | Dosing | Data |
|---|---|---|---|---|
| Group 11 | Sodium chloride deuterium oxide solution 0.4 ml/animal + 5-FU, 20 mg/kg | Giving drug for 3 days first, then giving drug on day 3, followed by inoculation | Then giving drug on each day for 10 days in total, then discontinuing the drug | Days that the animal had survived were recorded |

In Table 4, "Sodium chloride deuterium oxide solution 0.1 ml/animal+5-FU 20 mg/kg" means that each mouse was given 0.1 ml sodium chloride deuterium oxide solution, in which 5-FU had been dissolved to make a dose of 20 mg/kg.

3. Observation of Indicators

After the dosing, ascitic fluid was taken from 3 mice from each group, the volume of the ascitic fluid was measured, the number of tumor cells in the ascitic fluid was counted, and the rest of animals were continuously fed. Median survival time (MST) was recorded for animals in each group to evaluate the survival time for each group.

The comparison between the treatment group and the control group was expressed by T/C (%) which is calculated by the following equation:

$$T/C\% = \frac{T\ MST}{C\ MST} \times 100\%$$

T MST: MST of the treatment group; C MST: MST of the negative control group.

The evaluation criterion uses 125% as a cut-off threshold. When T/C %125%, effective, otherwise ineffective.

4. Statistics

The mean value was expressed in $\overline{X} \pm SD$. Inter-group analysis was statistically performed with t test. The results were statistically analyzed using SPSS (Statistical Package for the Social Science) 17.0.

5. Results 5.1. Survival time: effect of intraperitoneal administration of drugs on survival time (in days) of animals

TABLE 5

Effect of intraperitoneal administration of drugs on survival time (in days) of animals($\overline{X} \pm SD$, n = 8)

| Group | MST(days) | T/C(%) |
|---|---|---|
| control group: NS (0.4 ml/animal) | 14.1 ± 1.9 | |
| 5-FU (20 mg/kg)(in NS) | 21.8 ± 2.9* | 154.6% |
| 5-FU (30 mg/kg)(in NS) | 22.3 ± 4.9* | 158.1% |
| Sodium chloride deuterium oxide solution (0.4 ml/animal) | 17.2 ± 3.2** | 121.9% |
| Sodium chloride deuterium oxide solution (0.1 ml/animal) + 5-FU (20 mg/kg) | 21.4 ± 3.1* | 151.7% |
| Sodium chloride deuterium oxide solution (0.2 ml/animal) + 5-FU (20 mg/kg) | 24.1 ± 2.7* | 170.9% |
| Sodium chloride deuterium oxide solution (0.4 ml/animal) + 5-FU (20 mg/kg) | 25.7 ± 2.6* | 182.2% |

TABLE 5-continued

Effect of intraperitoneal administration of drugs on survival time (in days) of animals($\overline{X} \pm SD$, n = 8)

| Group | MST(days) | T/C(%) |
|---|---|---|

Compared to the control group:
*P < 0.001,
**P < 0.05.

TABLE 6

Effect of intraperitoneal lavage with sodium chloride deuterium oxide solution, followed by intraperitoneal administration of drugs, on survival time (in days) of animals (X ± SD, n = 8)

| Group | MST(days) | T/C(%) |
|---|---|---|
| control group: NS (0.4 ml/animal) | 15.3 ± 1.9 | |
| Sodium chloride deuterium oxide solution (0.1 ml/animal) + 5-FU (20 mg/kg) | 26.1 ± 3.7* | 170.5% |
| Sodium chloride deuterium oxide solution (0.2 ml/animal) + 5-FU (20 mg/kg) | 29.1 ± 3.1* | 190.1% |
| Sodium chloride deuterium oxide solution (0.4 ml/animal) + 5-FU (20 mg/kg) | 34.5 ± 3.3* | 225.4% |

Compared to the control group:
*P < 0.001.

The results demonstrate that, as compared to the NS control group, the group receiving combined sodium chloride deuterium oxide solution, and 5-FU showed an extended MST, with a P value<0.01 and T/C (%)≥150%, which was also better than the group receiving 5-FU alone.

Intraperitoneal lavage with the sodium chloride deuterium oxide solution first, followed by intraperitoneal administration of drugs, can achieve a significantly extended MST in mice, longer than the MST resulting from only intraperitoneal administration of drugs in the sodium chloride deuterium oxide solution, namely 29.1±3.1 days vs. 24.1+2.7 days; and 34.5±3.3 days vs. 25.7±2.6 days, both having a P value<0.05, demonstrating an advantage of intraperitoneal lavage with deuterium oxide followed by administration of drugs.

Example 20

Inhibition of liver cancer H22 ascites tumor in tumor-bearing mice by 42±1° C. hyperthermic intraperitoneal retention lavage using deuterium oxide in combination with cisplatin, and using deuterium oxide (42° C.) in combination with cisplatin.

Experimental Method

Animal: 4 to 5 week-aged male Kunming mice, provided by Shanghai SIPPR-BK Laboratory Animal Co. Ltd.

Cell lines: Liver cancer H22 ascites tumor cell line was provided by NANJING KEYGEN BIOTECH. CO., LTD.

Modeling: 0.2 ml suspension of H22 tumor cells containing $1\times10^7$ cells/ml ($2\times10^6$ H22 cells in total) was inoculated into the peritoneal cavity of mice.

Test drugs: cisplatin, and the Ringer's deuterium oxide solution as prepared in Example 6.

Grouping and dosing: the mouse model was established 7 to 8 days after inoculation, and the mice were randomized with 18 animals/group.

Cisplatin were dissolved in a 42±1° C. Ringer's deuterium oxide solution, and used to lavage the peritoneal cavity of the tumor-bearing mice.

1). Blank control group (normal Ringer's solution, 10 ml/kg, room temperature);
2). Normal chemo group (cisplatin 0.6 mg/kg+normal Ringer's solution, 10 ml/kg, room temperature);
3). Room temperature low-dose deuterium oxide+cisplatin group (Ringer's deuterium oxide solution, 5 ml/kg+cisplatin 0.6 mg/kg);
4). Room temperature mid-dose deuterium oxide+cisplatin group (Ringer's deuterium oxide solution, 20 ml/kg+cisplatin 0.6 mg/kg);
5). Room temperature high-dose deuterium oxide+cisplatin group (Ringer's deuterium oxide solution, 40 ml/kg+cisplatin 0.6 mg/kg);
6). Hyperthermic low-dose deuterium oxide+cisplatin group (42±1° C. Ringer's deuterium oxide solution, 5 ml/kg+cisplatin 0.6 mg/kg);
7). Hyperthermic mid-dose deuterium oxide+cisplatin group (42±1° C. Ringer's deuterium oxide solution, 20 ml/kg+cisplatin 0.6 mg/kg);
8). Hyperthermic high-dose deuterium oxide+cisplatin group (42±1° C. Ringer's deuterium oxide solution, 40 ml/kg+cisplatin 0.6 mg/kg);

The peritoneal cavity of mice was lavaged with the above compositions which were retained for 10 min in the peritoneal cavity after being introduced, which was repeated for 3 times. The lavage was performed once another day for 5 successive times. The body weight and abdomen circumference of mice were measured on each day before administration of the drugs, and the daily living status of mice was observed. 24 hours after the administration of drugs was completed (on day 11), 8 mice from each group were sacrificed, the volume of ascitic fluid was measured, and bodies of the mice were dissected to observe the peritonea organs and metastasis to lung. The rest of mice were observed for their survival time, and the extension of life was calculated.

4. Observation of indicators: the same as Example 19.
5. Statistics: the same as Example 19.
6. Results

TABLE 7

Effect of 42 ± 1° C. intraperitoneal lavage with deuterium oxide in combination with cisplatin on survival time (in days) of animals ($\overline{X}$ ± SD, n = 10)

| Group | MST (days) | T/C (%) |
|---|---|---|
| Blank control group (Ringer's solution for injection, 5 ml/kg) | 13.2 ± 1.9 | |
| Normal chemo group (cisplatin 0.6 mg/kg + Ringer's solution5 ml/kg) | 18.1 ± 3.2* | 137.1 |
| RT low-dose deuterium oxide + cisplatin group (Ringer's deuterium oxide solution5 ml/kg + cisplatin 0.6 mg/kg) | 20.3 ± 2.2* | 153.7 |
| RT mid-dose deuterium oxide + cisplatin group (Ringer's deuterium oxide Solution 20 ml/kg + cisplatin 0.6 mg/kg) | 24.7 ± 1.8* | 187.1 |
| RT high-dose deuterium oxide + cisplatin group (Ringer's deuterium oxide solution 40 ml/kg + cisplatin 0.6 mg/kg) | 26.1 ± 5.9* | 197.7 |
| Hyperthermic low-dose deuterium oxide + cisplatin group (Ringer's deuterium oxide solution 5 ml/kg + cisplatin0.6 mg/kg) | 24.3 ± 3.3* | 184.0 |
| Hyperthermic mid-dose deuterium oxide + cisplatin group (Ringer's deuterium oxide solution20 ml/kg + cisplatin0.6 mg/kg) | 28.6 ± 6.4* | 216.6 |
| Hyperthermic high-dose deuterium oxide + cisplatin group (Ringer's deuterium oxide solution40 ml/kg + cisplatin0.6 mg/kg) | 32.1 ± 3.1* | 243.1 |

Compared to the negative control group:
*P < 0.001.
RT means room temperature.

TABLE 8

Effect of 42 ± 1° C. intraperitoneal lavage with deuterium oxide in combination with cisplatinon the volume of ascitic fluid ($\overline{X}$ ± SD, n = 8)

| Groups | Ascitic fluid (ml) |
|---|---|
| Blank control group (Ringer's solution for injection, 5 ml/kg) | 14.85 ± 2.56 |
| Normal chemo group (cisplatin 0.6 mg/kg + Ringer's solution for injection 5 ml/kg) | 7.30 ± 2.32* |
| RT low-dose deuterium oxide + cisplatin group (Ringer's deuterium oxide solution 5 ml/kg + cisplatin 0.6 mg/kg) | 6.55 ± 3.95* |
| RT mid-dose deuterium oxide + cisplatin group (Ringer's deuterium oxide solution 20 ml/kg + cisplatin 0.6 mg/kg) | 4.93 ± 3.05* |
| RT high-dose deuterium oxide + cisplatin group (Ringer's deuterium oxide solution 40 ml/kg + cisplatin 0.6 mg/kg) | 4.08 ± 1.22* |
| Hyperthermic low-dose deuterium oxide + cisplatin group (Ringer's deuterium oxide solution 5 ml/kg + cisplatin0.6 mg/kg); | 3.11 ± 0.56** |
| Hyperthermic mid-dose deuterium oxide + cisplatin group (Ringer's deuterium oxide solution20 ml/kg + cisplatin0.6 mg/kg); | 2.49 ± 0.62** |

TABLE 8-continued

Effect of 42 ± 1° C. intraperitoneal lavage with deuterium oxide in combination with cisplatinon the volume of ascitic fluid ($\overline{X}$ ± SD, n = 8)

| Groups | Ascitic fluid (ml) |
|---|---|
| Hyperthermic high-dose deuterium oxide + cisplatin group (Ringer's deuterium oxidesolution40 ml/kg + cisplatin0.6 mg/kg) | 0.44 ± 0.46** |

Compared to the negative control group:
*P < 0.001,
**P < 0.0001.
RT means room temperature.

Cisplatin is a representative anti-tumor platinum preparation, and deuterium oxide has a broad-spectrum effect of enhancing anti-tumor efficacy. The results-demonstrate that the 42° C. hyperthermic intraperitoneal lavage with deuterium oxide in combination with cisplatin could significantly extend the survival time, inhibit production of ascitic fluid than deuterium oxide under room temperature in mice bearing H22 ascites tumors. The application of hyperthermic deuterium oxide exhibits an unexpected anti-tumor effect of enhancing, thereby improves quality of life of the tumor-bearing mice.

Example 21

Inhibition of sarcoma S180 (ascites type) in tumor-bearing mice by 42±1° C. hyperthermic intraperitoneal retention lavage using deuterium oxide in combination with oxaliplatin and using deuterium oxide in combination with oxaliplatin and mitomycin.

Experimental Method

Animal: 4 to 5 week-aged male Kunming mice, provided by Shanghai SIPPR-BK Laboratory Animal Co. Ltd.
Cell lines: sarcoma S180 (ascites type) cell line was provided by NANJING KEYGEN BIOTECH CO., LTD.
Modeling: 0.2 ml suspension of sarcoma S180 cells containing $1 \times 10^7$ cells/ml was inoculated into the peritoneal cavity of mice.
Test drugs: oxaliplatin, mitomycin, and the glucose deuterium oxide solution as prepared in Example 2.
Grouping and dosing: the mouse model was established 7 to 8 days after inoculation, and the mice were randomized with 12 animals/group.
Oxaliplatin and mitomycin were dissolved in a 42±1° C. glucose deuterium oxide solution, and used to lavage the peritoneal cavity of the tumor-bearing mice.
1). Blank control group (5% glucose injection, 5 ml/kg);
2). Chemo group (oxaliplatin 0.8 mg/kg+5% glucose injection, 5 ml/kg);
3). Low-dose deuterium oxide+oxaliplatin group (5% glucose deuterium oxide solution, 5 ml/kg+oxaliplatin 0.8 mg/kg);
4). Mid-dose deuterium oxide+oxaliplatin group (5% glucose deuterium oxide solution, 20 ml/kg+oxaliplatin 0.8 mg/kg);
5). High-dose deuterium oxide+oxaliplatin group (5% glucose deuterium oxide solution, 40 m/kg+oxaliplatin 0.8 mg/kg);
6). Low-dose deuterium oxide+oxaliplatin+mitomycin group (42±1° C. 5% glucose deuterium oxide solution, 5 ml/kg+oxaliplatin 0.8 mg/kg+mitomycin 0.4 mg/kg);
7). Mid-dose deuterium oxide+oxaliplatin+mitomycin group (42±1° C. 5% glucose deuterium oxide solution, 20 ml/kg+oxaliplatin 0.8 mg/kg+mitomycin 0.4 mg/kg);
8). High-dose deuterium oxide+oxaliplatin+mitomycin group (42±1° C. 5% glucose deuterium oxide solution, 40 ml/kg+oxaliplatin 0.8 mg/kg+mitomycin 0.4 mg/kg).

The peritoneal cavity was lavaged with the 42±1° C. glucose deuterium oxide solution in combination with the above composition, which were retained for 10 min in the peritoneal cavity after being introduced, which was repeated for 3 times. The lavage was performed once another day for 5 successive times. The body weight and abdomen circumference of mice were measured on each day before administration of the drugs, and the daily living status of mice was observed. 24 hours after the administration of drugs was completed (on day 11), 4 mice from each group were sacrificed, the volume of ascitic fluid was measured, and bodies of the mice were dissected to observe the peritoneal organs and metastasis to lung. The rest of mice were observed for their survival time, and the extension of life was calculated.
4. Observation of indicators: the same as Example 19.
5. Statistics: the same as Example 19.
6. Results

TABLE 9

Effect of 42 ± 1° C. intraperitoneal lavage with deuterium oxide in combination with oxaliplatin and mitomycin on survival time (in days) of animals ($\overline{X}$ ± SD, n = 8)

| Group | MST (days) | T/C (%) |
|---|---|---|
| Blank control group (glucose injection, 5 ml/kg) | 12.2 ± 3.0 | |
| Chemo group (oxaliplatin 0.8 mg/kg + glucose injection 5 ml/kg) | 21.7 ± 2.8* | 177.6 |
| Low-dose deuterium oxide + oxaliplatin(glucose deuterium oxide solution 5 ml/kg + oxaliplatin 0.8 mg/kg) | 23.4 ± 3.2* | 191.8 |
| Mid-dose deuterium oxide + oxaliplatin(glucose deuterium oxide solution 20 ml/kg + oxaliplatin 0.8 mg/kg) | 27.7 ± 4.9* | 227.0 |
| High-dose deuterium oxide + oxaliplatin (glucose deuterium oxide solution 40 ml/kg + oxaliplatin 0.8 mg/kg) | 31.1 ± 6.1* | 254.9 |
| Low-dose deuterium oxide + oxaliplatin + mitomycin(glucose deuterium oxide solution 5 ml/kg + oxaliplatin 0.8 mg/kg + mitomycin 0.4 mg/kg) | 26.4 | 216.3 |
| Mid-dose deuterium oxide + oxaliplatin + mitomycin(glucose deuterium oxide solution 20 ml/kg + oxaliplatin 0.8 mg/kg + mitomycin 0.4 mg/kg) | 30.1 | 246.7 |

TABLE 9-continued

Effect of 42 ± 1° C. intraperitoneal lavage with deuterium oxide in combination with oxaliplatin and mitomycin on survival time (in days) of animals ($\bar{X}$ ± SD, n = 8)

| Group | MST (days) | T/C (%) |
|---|---|---|
| High-dose deuterium oxide + oxaliplatin + mitomycin(glucose deuterium oxide solution 40 ml/kg + oxaliplatin 0.8 mg/kg + mitomycin 0.4 mg/kg) | 32.8 | 268.8 |

Compared to the negative control group: *P < 0.001.

TABLE 10

Effect of 42 ± 1° C. intraperitoneal lavage with deuterium oxide in combination with oxaliplatin and mitomycin on the volume of ascitic fluid ($\bar{X}$ ± SD, n = 8)

| Group | Ascitic fluid (ml) |
|---|---|
| Blank control group (glucose injection, 5 ml/kg) | 16.5 ± 4.3 |
| Chemo group (oxaliplatin 0.8 mg/kg + glucose injection 5 ml/kg) | 8.7 ± 1.9* |
| Low-dose deuterium oxide + oxaliplatin (oxaliplatin 0.8 mg/kg + glucose deuterium oxide solution 5 ml/kg) | 8.1 ± 2.8* |
| Mid-dose deuterium oxide + oxaliplatin (oxaliplatin 0.8 mg/kg + glucose deuterium oxide solution 20 ml/kg) | 7.3 ± 2.9* |
| High-dose deuterium oxide + oxaliplatin (oxaliplatin 0.8 mg/kg + glucose deuterium oxide solution 40 ml/kg) | 2.1 ± 1.3** |
| Low-dose deuterium oxide + oxaliplatin + mitomycin (oxaliplatin 0.8 mg/kg + mitomycin 0.4 mg/kg + glucose deuterium oxide solution 5 ml/kg) | 7.5 ± 3.1* |
| Mid-dose deuterium oxide + oxaliplatin + mitomycin (oxaliplatin 0.8 mg/kg + mitomycin 0.4 mg/kg + glucose deuterium oxide solution 20 ml/kg) | 3.7 ± 1.6** |
| High-dose deuterium oxide + oxaliplatin + mitomycin (oxaliplatin 0.8 mg/kg + mitomycin 0.4 mg/kg + glucose deuterium oxide solution 40 ml/kg) | 1.1 ± 0.5** |

Compared to the negative control group: * P< 0.005, **P < 0 001.

Oxaliplatin is a third-generation anti-tumor platinum preparation, mitomycin is an anti-tumor antibiotic to which tumor cells in GO to S phases are sensitive, and deuterium oxide has a broad-spectrum effect of enhancing anti-tumor efficacy, to which tumor cells in the S phase are also sensitive. Their combination can further enhance anti-tumor efficacy. The results demonstrate that the hyperthermic deuterium oxide in combination with oxaliplatin and mitomycin can also significantly extend the survival time of mice bearing sarcoma S180, and inhibits production of ascitic fluid in mice bearing sarcoma S180. This indicates that combination of hyperthermic deuterium oxide with platinum preparation and anti-tumor antibiotics has general applicability in inhibition of growth of various tumors.

Example 22

Inhibition of growth of xenograft tumors from human colon cancer HCT-166 cells in nude mice by intravenous injection of deuterium oxide in combination with 5-fluorouracil Animal: 6 to 7 week-aged female BALB/c nude mice, each weighing 18 to 20 g, provided by Shanghai SLAC Laboratory Animal Co. Ltd.

Cell lines: human colon cancer cells HCT-116 were provided by NANJING KEYGEN BIOTECH. CO., LTD.

Test drugs: 5-fluorouracil (5-FU), and the glucose (5%) deuterium oxide solution (containing 5 g glucose per 100 ml) prepared in Example 2.

Experimental Method

1. Modeling

Tumor cells were resuscitated and cultured according to a routine procedure, a suspension of cultured HCT-116 cells was collected, sterile sodium chloride physiological solution was added thereto to make a suspension at a concentration of $1 \times 10^7$ cells/ml, and 0.1 ml of the suspension was subcutaneously inoculated into the right axillary fossa of each nude mouse.

2. Grouping and Dosing Scheme

The diameter of xenograft tumors in the nude mice was measured with a vernier caliper, and 10 days after inoculation, when tumors grew to 100 to 110 cm$^3$, the animals were randomized with 8 mice per group. Meanwhile drugs were administered by injection into tail vein, once every three days, for 21 successive days. By measuring the tumor diameter, the anti-tumor efficacy of test samples was dynamically observed, and the body weight of animals was also recorded to observe the toxicity of the test samples. 21 days after administration, the nude mice were sacrificed, and tumors were harvested by surgery, weighed and photographed. Bone marrow nucleated cells were isolated by a routine method, DNA was extracted from the cells, the OD value was measured in a UV-260 spectrometer as a representative of the DNA content, and inhibition of DNA synthesis by the test samples was observed.

The test used 7 groups in total, with 8 animals per group.
1) Negative control group: 5% glucose injection, 10 ml/kg;
2) Paclitaxel positive control group: paclitaxel (8 mg/kg) diluted in sodium chloride physiological solution;
3) High-dose 5-FU positive control group: 5-FU (30 mg/kg) diluted in 5% glucose injection;
4) Low-dose 5-FU positive control group: 5-FU (12 mg/kg) diluted in 5% glucose injection.
5) Test group 1: 5-FU (12 mg/kg) diluted in the glucose deuterium oxide solution (5 mi/kg).
6) Test group 2: 5-FU (12 mg/kg) diluted in the glucose deuterium oxide solution (10 ml/kg).
7) Test group 3: 5-FU (12 mg/kg) diluted in the glucose deuterium oxide solution (20 ml/kg).

3. Observation of Indicators

1) Anti-tumor activity evaluation by relative tumor volume Tumor volume (TV) was calculated by the following equation:

TV=1/2×a×b$^2$, wherein $a$ and $b$ refer to length and width, respectively.

From the measurements, relative tumor volume (RTV) was calculated by the following equation:

RTV=$V_t/V_0$ wherein $V_0$ is the tumor volume measured on initial administration (i.e. do), and $V_t$ is the tumor volume measured each time afterwards.

Relative tumor growth ratio T/C (% was calculated b the following equation:

$$T/C(\%) = \frac{T_{RTV}}{C_{RTV}} \times 100$$

$T_{RTV}$: RTV of the treatment group; $C_{RTV}$: RTV of the negative control group.

Criteria. of efficacy evaluation: T/C %>40%, not efficacious; T/C %≤40% and statistically P<0.05, efficacious.

2) Anti-tumor activity evaluation by tumor weight

Inhibition of tumor growth (% was calculated the following ion:

$$\text{Inhibition of tumor growth} = \frac{ATW_{NCG} - ATW_{DG}}{ATW_{NCG}} \times 100\%$$

$ATW_{NCG}$: Average tumor weight in negative control group $ATW_{DG}$: Average tumor weight in drug-dosed group Criteria of efficacy evaluation: Inhibition of tumor growth<40%, not efficacious; Inhibition of tumor growth≥40% and statistically P<0.05, efficacious.

3) Observation of drug's inhibition of bone marrow and monitoring of drug's toxicity based on bone marrow DNA content.

4. Statistics

The mean value was expressed in X̄±SD. Inter-group analysis was statistically performed with t test. The results were statistically analyzed using SPSS (Statistical Package for the Social Science) 17.0.

5. Results

Figure 5:
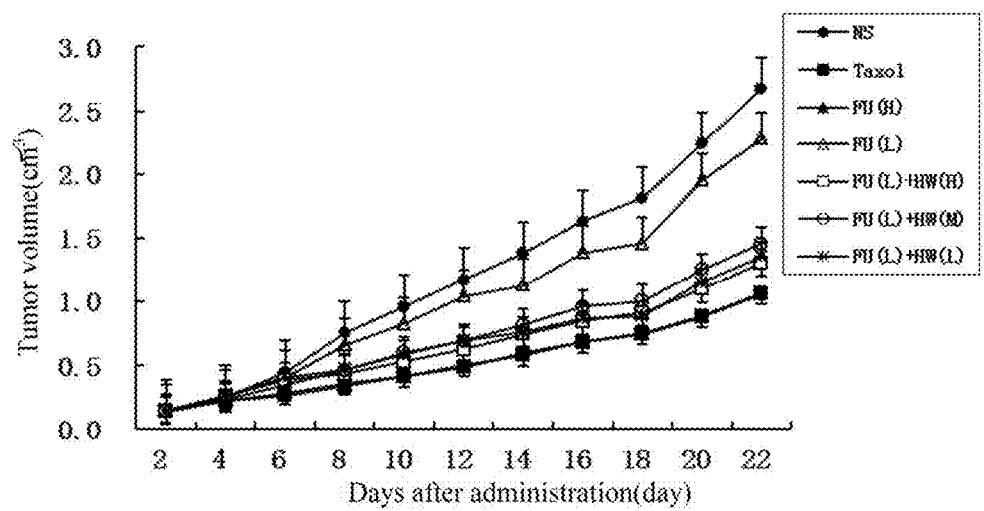
FIG. 5. Effect of the glucose deuterium oxide solution in combination with 5-FU on the tumor weight of xenograft tumors from human colon cancer HCT-166 cells in nude mice.

Anti-tumor activity evaluation by xenograft tumor volume: the results demonstrate that deuterium oxide in combination with low-dose 5-FU showed a good inhibitory effect on the xenograft tumors; 21 days after administration, the tumor volumes were 1.22±0.15 cm³ in the group receiving the deuterium oxide solution (5 ml/kg) in combination with 5-FU, 1.45±0.25 cm³ in the group receiving the deuterium oxide solution (10 ml/kg) in combination with 5-FU, and 1.27±0.24 cm³ in the group receiving the deuterium oxide solution (20 ml/kg) in combination with 5-FU, all with a T/C<40% as compared to the negative control group, and satisfied the criteria for pharmacological efficacy. But the group receiving low-dose 5-FU alone showed a reduced tumor volume to 2.27±0.30 cm³ only, with a T/C of 80.91%, which is >40% and did not satisfy the criteria for pharmacological efficacy. Therefore, when combined with 5-FU, deuterium oxide significantly enhance the anti-tumor efficacy of 5-FU, as shown in FIG. 5.

Figure 6:
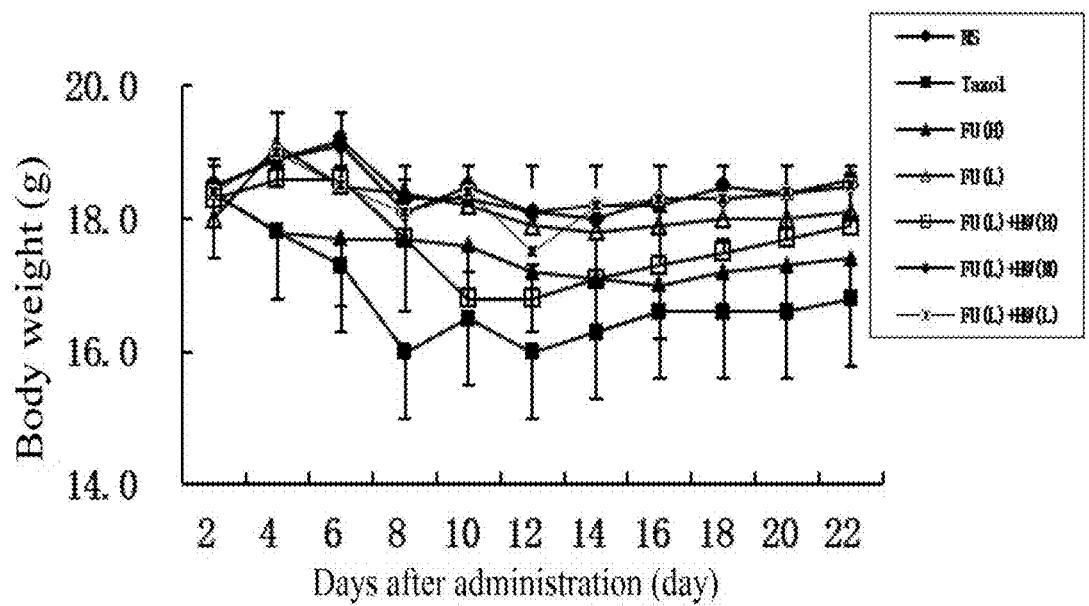
FIG. 6. Effect of the glucose deuterium oxide solution in combination with 5-FU on the body weight of nude mice bearing xenograft tumors from human colon cancer HCT-166 cells.

Anti-tumor activity evaluation by xenograft tumor weight the results demonstrate that deuterium oxide in combination with low-dose 5-FU showed a good inhibitory effect on the xenograft tumors; 21 days after administration, the inhibitions were 56.32% in the group receiving the deuterium oxide solution (5 ml/kg) in combination with 5-FU, 53.70% in the group receiving the deuterium oxide solution (10 mil/kg) in combination with 5-FU, and 54.22% in the group receiving the deuterium oxide solution (20 m/kg) in combination with 5-FU, all with a T/C>40% and P<0.001 as compared to the tumor weight in the negative control group, and all satisfied the criteria for pharmacological efficacy. The group receiving low-dose 5-FU alone showed an inhibition of 23.64% and did not satisfy the criteria for pharmacological efficacy. Therefore, when combined with 5-FU, deuterium oxide significantly enhance the anti-tumor efficacy of 5-FU, as shown in Table 11 and FIG. 6.

TABLE 11

Effect of deuterium oxide in combination with 5-FU on xenograft tumors from human colon cancer HCT-116 cells in nude mice (X̄ ± SD, n = 8)

| Group | Dose × Times | Body weight (g) (Initial/End) | Tumor weight (g) | Inhibition (%) | Bone marrow DNA content (OD) |
|---|---|---|---|---|---|
| Negative Control | 10 ml/kg | 18.5/+0.4 | 2.92 ± 0.27 | — | 0.950 ± 0.2711 |
| Paclitaxel positive control | 8 mg/kg × 11 | 18.4/−1.2 | 0.94 ± 0.25 | 67.80%* | 0.841 ± 0.3014** |
| 5-FU positive control 5-FU(H) | 30 mg/kg × 11 | 18.4/−1.0 | 1.04 ± 0.13 | 64.38%* | 0.836 ± 0.5023** |
| 5-FU low-dose 5-FU(L) | 12 mg/kg × 11 | 18.0/−0.6 | 2.23 ± 0.2 | 23.63% | 0.897 ± 0.3783** |
| Test group 1 5-FU(L) + HW(L) | Glucose deuterium oxide solution (5 ml/kg) + 5-FU (12 mg/kg) × 11 | 18.3/−0.4 | 1.34 ± 0.38 | 54.10%* | 0.913 ± 0.5122 |
| Test group 2 5-FU(L) + HW(M) | Glucose deuterium oxide solution(10 ml/kg) + 5-FU (12 mg/kg) × 11 | 18.5/+0.2 | 1.35 ± 0.34 | 53.76%* | 0.901 ± 0.4655 |

TABLE 11-continued

Effect of deuterium oxide in combination with 5-FU on xenograft tumors from human colon cancer HCT-116 cells in nude mice ($\overline{X} \pm SD$, n = 8)

| Group | Dose × Times | Body weight (g) (Initial/End) | Tumor weight (g) | Inhibition (%) | Bone marrow DNA content (OD) |
|---|---|---|---|---|---|
| Test group 3 5-FU(L) + HW(H) | Glucose deuterium oxide solution(20 ml/kg) + 5-FU (12 mg/kg) × 11 | 18.4/+0.2 | 1.28 ± 0.46 | 56.16%* | 0.921 ± 0.2910 |

Compared to the negative control group: *P < 0.001, **P < 0.05. Inhibition of tumor growth (%) > 40% indicates pharmacological efficacy.

Toxicity reduction: importantly, in the high-dose paclitaxel and 5-FU positive control groups, despite apparent inhibition of tumor growth, the body weight of tumor-bearing mice dropped greatly from 18.4±0.5 g to 16.8±0.9 g and to 17.4±0.5 g, respectively, and the bone marrow DNA content also decreased, indicating significant toxicity of paclitaxel and 5-FU to animals. The deuterium oxide solution in combination with 5-FU (10 mg/kg, one third of that of control) can achieve the same efficacy as high-dose paclitaxel and 5-FU (30 mg/kg) (equivalence), while the body weight of the tumor-bearing mice during dosing did not drop, and the bone marrow DNA content did not decrease, without the toxicity caused by high-dose paclitaxel and 5-FU. Because toxicity of anti-tumor drugs is very harmful to patients and even unacceptable to some weak or aged patients, chemotherapeutic drugs having low toxic side effects and a strong killing effect are urgently needed in tumor treatment. Hence, deuterium oxide in combination with 5-FU has a great advantage in clinical application, as shown in Table 11 and FIG. 7.

Example 23

Inhibition of growth of xenograft tumors from human ovarian cancer SKOV3 cells in nude mice by intravenous injection of deuterium oxide in combination with paclitaxel.

Animal: 6 to 7 week-aged female BALB/c nude mice, each weighing 18 to 20 g, provided by Shanghai SLAC Laboratory Animal Co. Ltd.

Cell lines: human ovarian cancer SKOV3 cells were provided by NANJING KEYGEN BIOTECH. CO., LTD.

Test drugs: paclitaxel and the sodium chloride deuterium oxide solution, prepared in Example 1.

Experimental Method

1. Tumor cell resuscitation and inoculation

Tumor cells were resuscitated and inoculated, and sterile sodium chloride physiological solution was added thereto to make a cell suspension which was subcutaneously inoculated into the upper right axillary fossa of animals. 5×10⁶ tumor cells were inoculated into each animal.

2. Grouping and dosing scheme

The diameter of xenograft tumors in the nude mice was measured with a vernier caliper, and 10 days after inoculation, when tumors grew to 100 to 110 cm$^3$, the animals were randomized. Meanwhile drugs were administered by injection into tail vein, once every three days, for 21 successive days. The body weight of animals was also recorded to observe the toxicity of the test samples. 21 days after administration, the nude mice were sacrificed, and tumors were harvested by surgery, and weighed.

The test used 6 groups in total, with 5 animals per group.

1) Control group: sodium chloride physiological solution, 10 m/kg;
2) Paclitaxel positive control group: paclitaxel (8 mg/kg) diluted in sodium chloride physiological solution;
3) Sodium chloride deuterium oxide solution (10 m/kg);
4) Test group 1: paclitaxel (8 mg/kg) diluted in the sodium chloride deuterium oxide solution (5 ml/kg);
5) Test group 2: paclitaxel (8 mg/kg) diluted in the sodium chloride deuterium oxide solution (10 ml/kg);
6) Test group 3: paclitaxel (8 mg/kg) diluted in the sodium chloride deuterium oxide solution (20 ml/kg).

3. Observation of indicators: the same as Example 22.

4. Statistics: the same as Example 22.

The results are shown in Table 12.

TABLE 12

Effect of sodium chloride deuterium oxide solution in combination with paclitaxel on tumor weight of xenograft tumors from human ovarian cancer SKOV3 cells in nude mice ($\overline{X} \pm SD$, n = 5)

| Group | Dose × Times | Body weight (g)(Initial/End) | Tumor weight (g) | Inhibition (%) |
|---|---|---|---|---|
| Control | 10 ml/kg | 20.8/+4.0 | 3.22 ± 1.59 | — |
| Paclitaxel | 8 mg/kg × 11 | 20.1/+2.8 | 2.07 ± 1.06 | 35.7 |
| Sodium chloride deuterium oxide solution | 10 ml/kg × 11 | 21.1/+3.9 | 2.44 ± 1.51 | 24.2 |
| Test group 1 Sodium chloride deuterium oxide solution + Paclitaxel | Sodium chloride deuterium oxide solution(5 ml/kg) + Paclitaxel(8 mg/kg) × 11 | 21.0/+3.8 | 1.95 ± 0.57 | 39.4 |
| Test group 2 Sodium chloride deuterium oxide solution + Paclitaxel | Sodium chloride deuterium oxide solution(10 ml/kg) + Paclitaxel(8 mg/kg) × 11 | 20.4/+3.7 | 1.71 ± 0.87 | 46.8* |

TABLE 12-continued

Effect of sodium chloride deuterium oxide solution in combination with paclitaxel on tumor weight of xenograft tumors from human ovarian cancer SKOV3 cells in nude mice ($\overline{X} \pm SD$, n = 5)

| Group | Dose × Times | Body weight (g)(Initial/End) | Tumor weight (g) | Inhibition (%) |
|---|---|---|---|---|
| Test group 3 Sodium chloride deuterium oxide solution + Paclitaxel | Sodium chloride deuterium oxide solution(20 ml/kg) + Paclitaxel(8 mg/kg) × 11 | 20.9/+4.1 | 1.45 ± 0.42 | 54.9* |

Compared to the control group: *P < 0.01.

Paclitaxel is an important phytogenic anti-tumor drug, having various types of a similar mechanism of action, including paclitaxel, paclitaxel liposomes, paclitaxel albumin, and docetaxel. The results demonstrate that, 21 days after administration, as compared to the control group, the groups receiving the deuterium oxide solution (10 ml/kg and 20 ml/kg) in combination with paclitaxel (8 mg/kg) showed a good inhibitory effect on xenograft tumors, with a significant reduction in tumor weight, while the tumor inhibition T/C was 54.9% on day 21 with P<0.001. On the other hand, as compared to the control group, the group receiving paclitaxel (8 mg/kg) alone showed a reduction, but did not satisfy the criteria of >40% for pharmacological efficacy. As compared to the control group, the group receiving the deuterium oxide solution (5 ml/kg) in combination with paclitaxel (12 mg/kg) showed a reduction, but did not satisfy the criteria of >40% for pharmacological efficacy. Deuterium oxide as a broad-spectrum anti-tumor efficacy-enhancing agent can also enhance the efficacy of phytogenic anti-tumor drugs.

Example 24

Inhibition of microvessel density of xenograft tumors from human pancreatic cancer PANC-1 cells in nude mice by intravenous injection of deuterium oxide in combination with bevacizumab.

Animal: 6 to 7 week-aged female BALB/c nude mice, each weighing 18 to 20 g, provided by Shanghai SLAC Laboratory Animal Co. Ltd.

Cell lines: human pancreatic cancer PANC-1 cells were provided by NANJING KEYGEN BIOTECH. CO., LTD.

Test drugs: bevacizumab (Avastin, Roche) and the sodium chloride deuterium oxide solution, prepared in Example 1.

Experimental Method

1. Modeling

Tumor cells were resuscitated and cultured according to a routine procedure, suspension of cultured PANC-1 cells was collected, sterile sodium chloride physiological solution was added thereto to make a suspension at a concentration of $1 \times 10^7$ cells/ml, and 0.1 ml of the suspension was subcutaneously inoculated into the right axillary fossa of each nude mouse.

2. Grouping and dosing scheme

The diameter of xenograft tumors in the nude mice was measured with a vernier caliper, and 10 days after inoculation, when tumors grew to 100 to 110 cm³, the animals were randomized. Meanwhile drugs were administered by injection into tail vein, once every three days, for 14 successive days. The body weight of animals was also recorded to observe the toxicity of the test samples. 14 days after administration, the dosing was discontinued for 1 week, then the nude mice were sacrificed, tumors were harvested by surgery and weighed, and the microvessel density (MVD) was examined. Tumors were stained by a standard EnVision™ method, the number of microvessels was counted by the Weidner microvessel method, the entire field was observed under 100× magnification, the areas having the highest microvessel density of the tumor were selected for counting, the microvessel density in three magnified fields was counted under 400× magnification, and the obtained values of microvessel density were averaged as the MVD.

The test used 4 groups in total, with 5 animals per group.
1) Negative control group: 0.9% sodium chloride injection, 10 m/kg;
2) Bevacizumab positive control group: bevacizumab (5 mg/kg) diluted in 0.9% sodium chloride injection;
3) Test group 1: bevacizumab (5 mg/kg) diluted in the sodium chloride deuterium oxide solution (10 ml/kg);
4) Test group 2: bevacizumab (5 mg/kg) diluted in the sodium chloride deuterium oxide solution (20 m/kg).
3. Observation of indicators: the same as Example 22.
4. Statistics: the same as Example 22.
5. Results: ne results are shown in Tables 13 and 14.

TABLE 13

Effect of deuterium oxide in combination with bevacizumab on tumor weight of xenograft tumors ($\overline{X} \pm SD$, n = 5)

| Groups | Tumor weight (g) | Inhibition of growth (%) |
|---|---|---|
| Negative control | 1.97 ± 0.29 | |
| Bevacizumab positive control | 1.12 ± 0.17* | 43.1 |
| Bevacizumab (5 mg/kg) diluted in sodium chloride deuterium oxide solution. (10 ml/kg) | 1.04 ± 0.13* | 47.2 |
| Bevacizumab (5 mg/kg) diluted in sodium chloride deuterium oxide solution. (20 ml/kg) | 0.93 ± 0.2* | 53.7 |

Compared to the negative control group: *P < 0.01.

TABLE 14

Effect of deuterium oxide in combination with bevacizumab on microvessel density (MVD)($\overline{X} \pm SD$, n = 5)

| Groups | MVD |
|---|---|
| Negative control | 31.10 ± 4.47 |
| Bevacizumab positive control | 22.40 ± 3.22* |
| Bevacizumab (5 mg/kg) diluted in sodium chloride deuterium oxide solution. (10 ml/kg) | 18.80 ± 1.58* |
| Bevacizumab (5 mg/kg) diluted in sodium chloride deuterium oxide solution. (20 ml/kg) | 16.60 ± 1.92* |

Compared to the negative control group: *P < 0.05.

Growth of tumor tissue requires a large amount of blood supply, and bevacizumab is an angiogenesis inhibitor. When the growth of microvessels in tumor tissue is inhibited, microvessels and blood supply are reduced. The results demonstrate that deuterium oxide as a broad-spectrum anti-tumor efficacy-enhancing agent can also enhance the effect of bevacizumab in reducing the microvessel density (MVD) in tumor tissue, reducing the blood supply to pancreatic cancer PANC-1 cells, and in turn inhibiting tumor growth.

Example 25

Comparison of survival time of nude mice bearing human colon cancer HCT-116 cells upon 42° C. hyperthermic intraperitoneal retention lavage using a hydroxyethyl starch deuterium oxide solution in combination with 5-FU and using a sodium chloride deuterium oxide solution in combination with 5-FU.

Experimental Method

Animal: 4 to 5 week-aged male nude mice, provided by Shanghai SIPPR-BK Laboratory Animal Co. Ltd.

Cell lines: human colon cancer cell line HCT-116 was provided by NANJING KEYGEN BIOTECH. CO., LTD.

Modeling: 0.2 ml suspension of HCT-116 cancer cells containing $1 \times 10^7$ cells/ml ($2 \times 10^6$ cells in total) was inoculated into the peritoneal cavity of the nude mice.

Test drugs: 5-FU, the 6% hydroxyethyl starch (200/0.5) deuterium oxide solution prepared in Example 10, and the 0.9% sodium chloride deuterium oxide solution, prepared in Example 1.

Grouping and dosing: the mouse model was established 7 to 8 days after inoculation into the nude mice, and the mice were randomized with 18 animals/group.

5-FU was separately dissolved in the hydroxyethyl starch deuterium oxide solution at 42° C., and in the sodium chloride deuterium oxide solution at 42° C., for intraperitoneal lavage of tumor-bearing mice.

1). Blank control group (42° C. sodium chloride physiological solution, 10 ml/kg);
2). Normal chemo group (42° C. sodium chloride physiological solution, 10 ml/kg+5-FU 20 mg/kg);
3). Low-dose sodium chloride deuterium oxide solution+5-FU group (42° C. sodium chloride deuterium oxide solution 5 ml/kg+5-FU 20 mg/kg);
4). Mid-dose sodium chloride deuterium oxide solution+5-FU group (42° C. sodium chloride deuterium oxide solution 20 ml/kg+5-FU 20 mg/kg);
5). High-dose sodium chloride deuterium oxide solution+5-FU group (42° C. sodium chloride deuterium oxide solution 40 ml/kg+5-FU 20 mg/kg);
6). Low-dose hydroxyethyl starch deuterium oxide solution+5-FU group (42° C. hydroxyethyl starch deuterium oxide solution, 5 ml/kg+5-FU 20 mg/kg);
7). Mid-dose hydroxyethyl starch deuterium oxide solution+5-FU group (42° C. hydroxyethyl starch deuterium oxide solution, 20 ml/kg+5-FU 20 mg/kg);
8). High-dose hydroxyethyl starch deuterium oxide solution+5-FU group (42° C. hydroxyethyl starch deuterium oxide solution, 40 ml/kg+5-FU 20 mg/kg).

The peritoneal cavity of nude mice was lavaged with the above compositions which were retained for 20 min in the peritoneal cavity after being introduced, which was performed once a day for 5 successive times. The body weight and abdomen circumference of the nude mice were measured on each day before administration of the drugs, and the daily living status of mice was observed. After administration of drugs was completed, 4 nude mice from each group were sacrificed, and bodies of the nude mice were dissected to observe the cancer cells and peritoneal organs. The rest of nude mice were observed for their survival time, and the extension of life was calculated.

4. Observation of indicators: the same as Example 18.
5. Statistics: the same as Example 18.

6. Results:

TABLE 15

Effect of 42° C. intraperitoneal lavage with hydroxyethyl starch deuterium oxide solution in combination with 5-FU on survival time (in days) of animals ($\overline{X} \pm SD$, n = 10)

| Groups | MST (days) | T/C (%) |
|---|---|---|
| Blank control group | 12.4 ± 2.9 | |
| Normal chemo group | 17.2 ± 2.2* | 138.7 |
| Low-dose sodium chloride deuterium oxide solution + 5-FU | 21.6 ± 2.5* | 174.1 |
| Mid-dose sodium chloride deuterium oxide solution + 5-FU | 23.2 ± 1.0* | 187.0 |
| High-dose sodium chloride deuterium oxide solution + 5-FU | 27.4 ± 4.4* | 220.9 |
| Low-dose hydroxyethyl starch deuterium oxide solution + 5-FU | 30.7 ± 4.3** | 247.5 |
| Mid-dose hydroxyethyl starch deuterium oxide solution + 5-FU | 38.6 ± 4.3** | 311.2 |
| High-dose hydroxyethyl starch deuterium oxide solution + 5-FU | 42.1 ± 4.7** | 339.5 |

Compared to the blank control group: *$P < 0.001$, **$P < 0.0001$.

In patients with mid-stage and late stage colon cancer, intraperitoneal metastasis often occurs, and the patients can survive only several months, and intraperitoneal lavage with anti-tumors drugs may have a certain effect thereon. The sodium chloride deuterium oxide solution, as an anti-tumors drug carrier, in which 5-FU is dissolved showed an anti-tumor efficacy-enhancing effect. However, deuterium oxide is a medium of small molecules, resides in the peritoneal cavity for only a short time, and is rapidly metabolized, thereby lowering the anti-tumors effect of 5-FU. Hydroxyethyl starch is a polymer excipients for drugs, shows a long retention time in blood, and now has been a regular plasma replacement in clinical settings.

The results demonstrate that the 42° C. hyperthermic intraperitoneal lavage using a hydroxyethyl starch deuterium oxide solution in combination with 5-FU can significantly extend the survival time of nude mice bearing colon cancer cell and enhance the anti-tumor efficacy, apparently superior to the intraperitoneal lavage using a sodium chloride deuterium oxide solution in combination with 5-FU.

Example 26

Effect of sodium bicarbonate deuterium oxide solution on model of transplanted liver cancer.

12 rabbits as a model of VX2 transplanted liver cancer were randomized into 3 groups (4 animals per group).

Group 1: Embolization treatment by hepatic arterial infusion with sodium chloride physiological solution 5 ml+5-FU (20 mg/kg)+ultra fluid lipiodol 0.5 ml;

Group 2: Embolization treatment by hepatic arterial infusion with 5% sodium bicarbonate solution 5 ml+5-FU (20 mg/kg)+ultra fluid lipiodol 0.5 ml;

Group 3: Embolization treatment by hepatic arterial infusion with 5% sodium bicarbonate deuterium oxide solution 5 ml+5-FU (20 mg/kg)+ultra fluid lipiodol 0.5 ml.

2 weeks after the operation, the laboratory rabbits were sacrificed and tumors were taken. The tumor growth rate was calculated by macro pathological examination, pathological examinations were performed by optical and electron microscopy, and comparative studies were made between the groups, the results shown in Table 16.

TABLE 16

Effect of sodium bicarbonate deuterium oxide solution on model of transplanted liver cancer

| Groups | Size (cm) | Tumor nodule | Formation of pseudo-capsule | Partial central necrosis in tumor nodule |
|---|---|---|---|---|
| Embolization with sodium chloride physiological solution + 5-FU (20 mg/kg) + lipiodol | 3 × 4 | Intact | No | Present, apparent |
| Embolization with sodium bicarbonate solution + 5-FU (20 mg/kg) + lipiodol | 2.0 × 0.9 | Non-intact | Yes | Absent |
| Embolization with sodium bicarbonate deuterium oxide solution + 5-FU (20 mg/kg) + lipiodol | 1.2 × 1 | Non-intact | No | Absent |

Analysis of various observed indices demonstrates that the group receiving embolization with sodium bicarbonate deuterium oxide solution+lipiodol is apparently better than the group receiving embolization with sodium chloride physiological solution or sodium bicarbonate solution+lipiodol, in terms of the degree of necrosis of tumors and the anti-tumors effect.

Example 27

Effect of 42° C. hyperthermic intraperitoneal retention lavage with hydroxypropyl-β-cyclodextrin (HP-β-CD) deuterium oxide solution in combination with gemcitabine (GEM) on the survival of nude mice bearing human pancreatic cancer PANC-1 cell.

Experimental Method

Animal: 4 to 5 week-aged male nude mice, provided by Shanghai SIPPR-BK Laboratory Animal Co. Ltd.
Cell lines: human pancreatic cancer PANC-1 cell line was provided by NANJING KEYGEN BIOTECK CO., LTD.
Modeling 0.2 ml suspension of pancreatic cancer PANC-1 cells containing 1×10$^7$ cells/ml (2×10$^6$ cells in total) was inoculated into the peritoneal cavity of the nude mice.
Test drugs: gemcitabine, the HP-β-CD deuterium oxide solution prepared in Example 12, and the 0.9% sodium chloride deuterium oxide solution prepared in Example 2.
Grouping and dosing: the mouse model was established 7 to 8 days after inoculation into the nude mice, and the mice were randomized with 18 animals/group.
Gemcitabine was separately dissolved in the HP-β-CD deuterium oxide solution at 42° C., and in the sodium chloride deuterium oxide solution at 42° C., for intraperitoneal lavage of tumor-bearing mice.
1). Blank control group (42° C. sodium chloride physiological solution, 10 ml/kg);
2). Normal chemo group (42° C. sodium chloride physiological solution, 10 ml/kg+gemcitabine 20 mg/kg);
3). Low-dose sodium chloride deuterium oxide solution+gemcitabine group (42° C. sodium chloride deuterium oxide solution, 5 ml/kg+gemcitabine 20 mg/kg);
4). Mid-dose sodium chloride deuterium oxide solution+gemcitabine group (42° C. sodium chloride deuterium oxide solution, 20 ml/kg+gemcitabine 20 mg/kg);
5). High-dose sodium chloride deuterium oxide solution+gemcitabine group (42° C. sodium chloride deuterium oxide solution, 40 ml/kg+gemcitabine 20 mg/kg);
6). Low-dose HP-β-CD deuterium oxide solution+gemcitabine group (42° C. HP-β-CD deuterium oxide solution 2.5 m/kg+gemcitabine 20 mg/kg);
7). Mid-dose HP-β-CD deuterium oxide solution+gemcitabine group (42° C. HP-β-CD deuterium oxide solution 5 ml/kg+gemcitabine 20 mg/kg);
8). High-dose HP-β-CD deuterium oxide solution+gemcitabine group (42° C. HP-γ-CD deuterium oxide solution 10 ml/kg+gemcitabine 20 mg/kg).

The peritoneal cavity of nude mice was lavaged with the above compositions which were retained for 20 min in the peritoneal cavity after being introduced, which was performed once a day for 5 successive times. The body weight and abdomen circumference of the nude mice were measured on each day before administration of the drugs, and the daily living status of mice was observed. After administration of drugs was completed, 4 nude mice from each group were sacrificed, and bodies of the nude mice were dissected to observe the cancer cells and peritoneal organs. The rest of nude mice were observed for their survival time, and the extension of life was calculated.
4. Observation of indicators: the same as Example 18.
5. Statistics: the same as Example 18.
6. Results

TABLE 17

Effect of 42° C. intraperitoneal lavage with HP-β-CD deuterium oxide solution in combination with gemcitabine on survival time (in days) of animals ($\bar{X} \pm SD$, n = 10)

| Groups | MST (days) | T/C (%) |
|---|---|---|
| Blank control group | 11.8 ± 2.2 | |
| Normal chemo group | 17.8 ± 1.8* | 150.8 |
| Low-dose sodium chloride deuterium oxide solution + GEM | 20.6 ± 2.2* | 174.5 |
| Mid-dose sodium chloride deuterium oxide solution + GEM | 22.2 ± 1.4* | 188.1 |
| High-dose sodium chloride deuterium oxide solution + GEM | 26.8 ± 4.4* | 227.1 |
| Low-dose HP-β-CD deuterium oxide solution + GEM | 29.7 ± 3.3** | 251.6 |
| Mid-dose HP-β-CD deuterium oxide solution + GEM | 41.6 ± 3.4** | 352.5 |
| High-dose HP-β-CD deuterium oxide solution + GEM | 46.2 ± 3.7** | 391.5 |

Compared to the blank control group: *P < 0.001, **P < 0.0001.

β-cyclodextrin is a cyclic oligosaccharide and useful as a drug stabilizer. HP-β-CD and sulfobutylether-β-cyclodextrin (SBE-β-CD) have similar properties, are both readily soluble in water, can also solubilize insoluble drugs, can control drug release, have good safety, and are suitable for preparation of lavage solutions and mucosa administrating systems.

In this experiment, the sodium chloride deuterium oxide solution as an anti-tumors drug carrier in which gemcitabine was dissolved showed an anti-tumor efficacy-enhancing effect. However, deuterium oxide is a medium of small molecules, resides in the peritoneal cavity for only a short time, and is rapidly metabolized, lowering the anti-tumors effect of gemcitabine. HP-β-CD shows a long retention time in blood, and slowly releases the gemcitabine dissolved therein. The results demonstrate that the 42° C. hyperthermicintraperitoneal lavage using a HP-β-CD deuterium oxide solution in combination with gemcitabine can significantly extend the survival time of nude mice bearing pancreatic cancer cell and enhance the anti-tumor efficacy, superior to the intraperitoneal lavage using a sodium chloride deuterium oxide solution in combination with gemcitabine, and only requires a small dose which is readily acceptable to patients.

Example 28

Intra-bladder perfusion and lavage experiment with the sodium hyaluronate deuterium oxide solution.

Four bladder cancer patients, diagnosed with superficial bladder cancer (SBC) by cystoscopy and pathological examination and having undergone transurethral resection of bladder tumor (TURBt), were subjected to intrabladder perfusion and lavage for 60 min with a 50 ml 0.08% sodium hyaluronate deuterium oxide solution which had been warmed to 43.5±1° C. in a hyperthermic perfusion and lavage apparatus (BR-TRG-1 hyperthermic perfusion intraperitoneal treatment system, manufactured by Baorui Medical Technology Co., Ltd, Guangzhou, China) and mixed with mitomycin (MMC, 40 mg/50 ml). The above procedure was carried out once a week for 6 successive weeks, and the following indices were observed:

(1) adverse reaction of bladder to chemotherapeutic drugs after perfusion: VAS score (pain), and hematuria;

(2) 12 months later, recurrence of bladder cancer was examined by cystoscopy, and the results are shown in Table 18.

TABLE 18

Effect of intra-bladder perfusion and lavage with the sodium hyaluronate deuterium oxide solution.

| No. | Gender | Age (years) | Tumor location | Tumor size/cm | VASscore | Hematuria | Recurrence |
|---|---|---|---|---|---|---|---|
| 1 | Male | 61 | Trigone | 0.2 × 0.2(3 tumors) | 0.12 | No | No |
| 2 | Male | 57 | Posterior wall | 0.5 × 0.3(1 tumor) | 0.11 | Occasional, in very small amounts | No |
| 3 | Female | 49 | Lateral walls | 0.2 × 0.2(6 tumors) | 0.16 | No | No |
| 4 | Male | 38 | Lateral walls | 0.1 × 0.1(8 tumors) | 0.22 | No | No |

When the anti-tumors drug mitomycin dissolved in only a sodium chloride solution is used for intra-bladder perfusion and lavage to treat SBC, urine stimulates the inner cavity of bladder and often causes great pain to patients because the anti-tumors drug damages the glucosamine protection layer lining the epithelium of the bladder cavity, which results in hematuria and cease of the treatment. Furthermore, the anti-tumors drug mitomycin has a short life in a sodium chloride solution, which reduces its effect and leads to a tumor recurrence rate as high as 78% and eventually to a failure of treatment. The sodium hyaluronate is a linear macromolecule and acid mucopolysaccharide, has excellent anti-inflammatory and anti-viscous performance, and can slow down drug release. When the sodium hyaluronate deuterium oxide solution is used for intrabladder perfusion, the sodium hyaluronate can temporarily play the role of the glucosamine protection layer lining the epithelium of the bladder and prolong the retention time of the anti-tumors drug mitomycin in bladder, while deuterium oxide also enhances the effect of mitomycin. Their combination can not only enhance the efficacy of the anti-tumors drug, but also reduce the side effects of the anti-tumors drug. The use of a 0.08% sodium hyaluronate deuterium oxide solution in combination with mitomycin for intrabladder hyperthermic perfusion and lavage in a preliminary treatment experiment has shown efficacy, in that the pain in patients was significantly reduced and no recurrence was seen within 12 months.

Example 29

Studies on drug safety: toxicity test for intravenous injection of sodium chloride deuterium oxide solution.

Experimental Method 6 to 7 week-aged SD rats, half male and half female, with males each weighing 280 to 338 g and females each weighing 212 to 268 g, were provided by Beijing Vital River Laboratory Animal Technology Co., Ltd.

Test sample: the sodium chloride deuterium oxide solution (abundance 99.9% b), prepared in Example 1.

Experiment 1: Observation of Toxicity after Single Dosing

Dosing scheme: A maximum dosing method was used, in which the sodium chloride deuterium oxide solution prepared in Example 1 was intravenously injected at a dose of 20 ml/kg into 20 rats, half male and half female, at an injection speed of 2 ml/min. An equal volume of a 0.9% sodium chloride rejection was given to the control group containing 10 rats, half male and half female.

TABLE 19

Dosing and grouping.

| Groups | Dose (mg/kg) | Drug volume (ml/100 g) | Number of animals | Serial No. of Male | Serial No. of Female |
|---|---|---|---|---|---|
| sodium chloride deuterium oxide solution | — | 2 | 20 | 1101-1110 | 2101-2110 |
| Control | 0* | 2 | 10 | 1001-1005 | 2001-2005 |

*indicates that an equal volume of a 0.9% sodium chloride rejection was given to the control group.

Experimental Results

1. Observation of General Symptoms

In the toxicity experiment in which a single dose of sodium chloride deuterium oxide solution was intravenously administered to rats, a maximum dose of 20 ml/kg was given to the subjects. Immediately after administration, animals receiving the test sample all showed symptoms such as reduced activity, shortness of breath, and increased urination, which were recovered to normal within 1 hour after the administration, and no other apparent abnormalities were found.

Observations were made at least once a day for 14 successive days, and no abnormalities in appearance and body sign, behavior and activity, and excrement characteristics or death was seen.

2. Body Weight

During the experiment, the animals showed a good general status and a normal increase in body weight.

TABLE 20

Body weight change of rats (male) in the toxicity experiment with single intravenous administration of sodium chloride deuterium oxide solution (g, $\overline{X} \pm SD$)

| Groups | 0 day(s) post administration | 7 day(s) post administration | 14 day(s) post administration |
|---|---|---|---|
| sodium chloride deuterium oxide solution | 304.40 ± 21.10 | 333.00 ± 21.47 | 360.50 ± 16.30 |
| Control | 309.40 ± 10.09 | 334.80 ± 9.58 | 364.40 ± 11.19 |

Note:
the group receiving sodium chloride deuterium oxide solution: n = 10; the control group: n = 5.

TABLE 21

Body weight change of rats (female) in the toxicity experiment with single intravenous administration of sodium chloride deuterium oxide solution (g, $\overline{X} \pm SD$)

| Groups | 0 day(s) post administration | 7 day(s) post administration | 14 day(s) post administration |
|---|---|---|---|
| sodium chloride deuterium oxide solution | 248.80 ± 17.08 | 264.20 ± 19.58 | 275.80 ± 19.45 |
| Control | 250.20 ± 6.22 | 267.60 ± 10.97 | 278.40 ± 11.72 |

Note:
the group receiving sodium chloride deuterium oxide solution: n = 10; the control group: n = 5.

Discussion: in the toxicity experiment in which a single dose of sodium chloride deuterium oxide solution, as the test sample was intravenously administered to rats, a maximum dose of 20 ml/kg of the sodium chloride deuterium oxide solution was given to the subjects. Immediately after administration, symptoms such as reduced activity and shortness of breath were observed, and no other toxicities associated with the test sample were found. Observations were continued for two weeks, the animals showed a normal increase in body weight, and no death was seen. According to the results of this experiment, for single-dose intravenous administration to rats, the minimum lethal dose (MLD) of the sodium chloride deuterium oxide solution, as the test sample is greater than 20 ml/kg.

Experiment 2: Observation of Toxicity During Multiple Dosing

Dosing scheme: A method of repeatedly administrating the maximum dose was used, in which the sodium chloride deuterium oxide solution, prepared in Example 1 was intravenously injected once a day at a dose of 20 ml/kg and an injection speed of 2 ml/min to 20 rats, half male and half female, for 5 successive days. An equal volume of a 0.9% sodium chloride rejection was given to the control group containing 10 rats, half male and half female.

TABLE 22

Dosing and grouping.

| Groups | Dose (mg/kg) | Drug volume (ml/100 g) | Number of animals | Serial No. of Male | Serial No. of Female |
|---|---|---|---|---|---|
| sodium chloride deuterium oxide solution | — | 2 × 5 times | 20 | 1201-1210 | 2201-2210 |
| Control | 0* | 2 × 5 times | 10 | 1101-1105 | 2101-2105 |

*indicates that an equal volume of a 0.9% sodium chloride rejection was given to the control group.

Experimental Results

1. Observation of General Symptoms

In the toxicity experiment in which multiple doses of sodium chloride deuterium oxide solution were intravenously administered to rats, a maximum dose of 20 ml/kg was given to the subjects once a day, for 5 successive days. Immediately after each administration, animals receiving the test sample all showed symptoms such as reduced activity, shortness of breath, and increased urination, which were recovered to normal within 1 hour after the administration, and no other apparent abnormalities were found.

Observations were made at least once a day for 3 successive months, and no abnormalities in appearance and body sign, behavior and activity, and excrement characteristics or death was seen.

2. Body Weight

During the experiment, the animals showed a good general status and a normal increase in body weight.

TABLE 23

Body weight change of rats (male) in the toxicity experiment with multiple repeating intravenous administration of sodium chloride deuterium oxide solution (g, $\overline{X} \pm SD$)

| Groups | 0 day(s) post administration | 30 day(s) post administration | 90 day(s) post administration |
|---|---|---|---|
| sodium chloride deuterium oxide solution | 305.20 ± 20.90 | 352.00 ± 31.72 | 452.40 ± 30.14 |
| Control | 303.20 ± 11.10 | 361.01 ± 29.65 | 461.91 ± 31.19 |

Note:
the group receiving sodium chloride deuterium oxide solution: n = 10; the control group: n = 5.

TABLE 24

Body weight change of rats (female) in the toxicity experiment with multiple repeating intravenous administration of sodium chloride deuterium oxide solution (g, x̄ ± SD)

| Groups | 0 day(s) post administration | 30 day(s) post administration | 90 day(s) post administration |
|---|---|---|---|
| sodium chloride deuterium oxide solution | 243.52 ± 14.88 | 293.20 ± 18.83 | 395.63 ± 29.54 |
| Control | 251.28 ± 11.22 | 298.12 ± 14.67 | 405.42 ± 26.12 |

Note:
the group receiving sodium chloride deuterium oxide solution: n = 10; the control group: n = 5.

In the toxicity experiment in which multiple doses of sodium chloride deuterium oxide solution, as the test sample were repeatedly intravenously administered to rats, a maximum dose of 20 ml/kg of the sodium chloride deuterium oxide solution was given to the subjects. Immediately after administration, symptoms such as reduced activity and shortness of breath were observed, and no other toxicities associated with the test sample were found. Observations were continued for 3 months, the animals showed a normal increase in body weight, and no death was seen. According to the results of this experiment, for multiple-dose intravenous administration to rats, the minimum lethal dose (MLD) of the sodium chloride deuterium oxide solution, as the test sample is greater than 20 ml/kg.

Example 30

Effect of deuterium oxide reduced the toxicity of gemcitabine in the tumor cell bearing mice model.

Gemcitabine (GEM), a chemotherapy drug, attack tumor cells, but can also damage the other normal cells and microstructures of an organism, such as bone morrow cells, liver cells. This study explored whether deuterium oxide could reduce the toxicity of GEM in the tumor cell bearing mice model.

Experimental Method

Animal: 6 to 7 week-aged female BALB/c nude mice, each weighing 18 to 20 g, provided by Shanghai SLAC Laboratory Animal Co. Ltd.

Cell lines: human pancreatic cancer cells CFPAC-1 were provided by NANJING KEYGEN BIOTECH CO., LTD.

Test drugs: Gemcitabine (GEM), deuterium oxide injection prepared in Example 1.

Modeling and Dosing Scheme

Tumor cells were resuscitated and cultured according to a routine procedure, a suspension of cultured CFPAC-1 cells was collected, sterile sodium chloride physiological solution was added thereto to make a suspension at a concentration of $1 \times 10^7$ cells/ml, and 0.1 ml of the suspension was subcutaneously inoculated into the right axillary fossa of each nude mouse.

The diameter of xenograft tumors in the nude mice was measured with a vernier caliper, and 10 days after inoculation, when tumors grew to 100 to 110 cm$^3$. The mice were randomly divided into 4 groups (n=7/group). The control group was injected with saline. The GEM group was injected into the tail vein with a dose of 80 mg/kg, once per-week, 4 weeks. The deuterium oxide group was treated with deuterium oxide injection per-day administered. The deuterium oxide+GEM group was treated with GEM 80 mg/kg and deuterium oxide administered.

1) control group: saline solution injection, 10 ml/kg;
2) deuterium oxide group: deuterium oxide injection, 30 g/kg;
3) deuterium oxide group: deuterium oxide injection, 20 g/kg
4) GEM group: GEM (80 mg/kg) diluted in saline solution;
5) GEM group: GEM (40 mg/kg) diluted in saline solution;
6) GEM group: GEM (20 mg/kg) diluted in saline solution;
7) GEM+deuterium oxide group: GEM (80 mg/kg) diluted in deuterium oxide injection (20 g/kg).
8) GEM+deuterium oxide group: GEM (40 mg/kg) diluted in deuterium oxide injection (20 g/kg).
9) GEM+deuterium oxide group: GEM (20 mg/kg) diluted in deuterium oxide injection (20 g/kg).

The drugs were administered by injection into tail vein, for 28 successive days. By measuring the tumor diameter, the anti-tumor efficacy of test samples was dynamically observed. After administration, the nude mice were sacrificed, and tumors were harvested by surgery, weighed and photographed.

TABLE 25 deuterium oxide enhanced the anti-tumor effect of GEM.

| Control | HW 30 g/kg | HW 20 g/kg | GEM 80 mg/kg | GEM 40 mg/kg | GEM 20 nmg/kg | GEM + HW 80 mg/kg + 20 g/kg | GEM + HW 40 mg/kg + 20 g/kg | GEM + HW 20 mg/kg + 20 g/kg |
|---|---|---|---|---|---|---|---|---|
| 2.45 ± 0.23 | 2.32 ± 0.28 | 2.3 ± 0.17 | 0.61 ± 0.12* | 0.88 ± 0.14 | 1.03 ± 0.11 | 0.38 ± 0.10 | 0.61 ± 0.15 | 0.83 ± 0.11# | n = 7,
*$P < 0.05$, compared with control group;
$P < 0.05$, compared with GEM group;

Blood was collected from the orbital artery at 28 days, and white blood cells (WBC) were counted using a hemocytometer to observe the haematopoietic cells function. Alanine aminotransferase (ALT) and aspartate aminotransferase (AST) in the serum were measured as the hepatotoxicity biomarker.

Results

Figure 7:
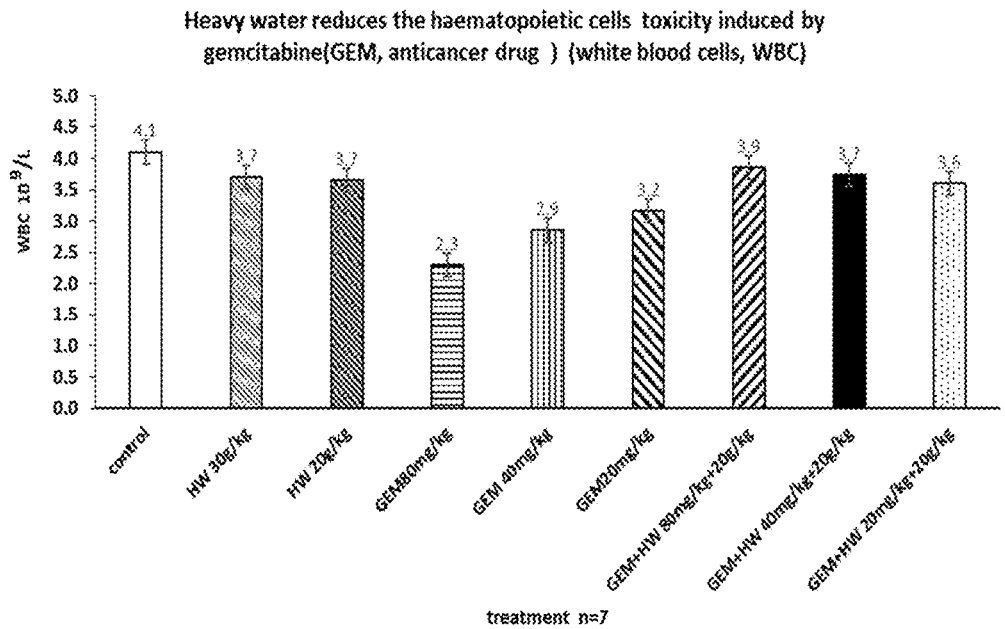
FIG. 7: Deuterium oxide reduced the haematopoietic cells toxicity of GEM, WBC as biomarker.

WBC. In the present study, alterations in the WBC count were found in all groups (FIG. 7). No remarkable difference in the number of WBC was observed between the deuterium oxide group and control group while that in the GEM group was significantly ($P<005$) lower than that in the control group, 2.3 10$^9$/L v.s. 4.1 10$^9$/L. All of the deuterium oxide treatments ($P<005$) could significantly enhance the recovery of the WBC to normal level in GEM mice.

Figure 8:
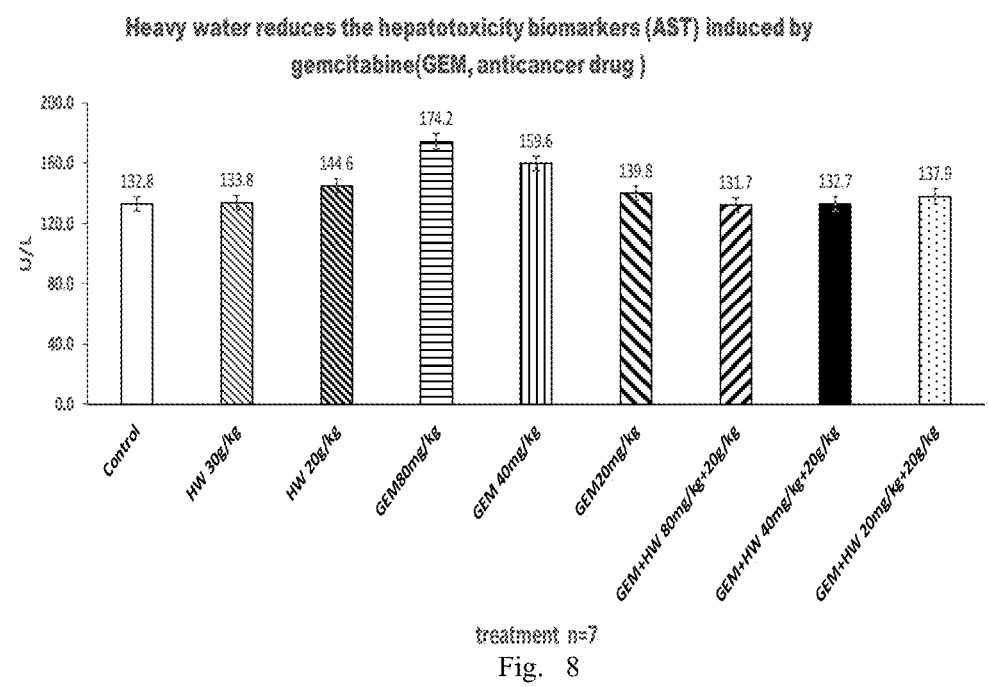
FIG. 8: Deuterium oxide reduced the liver cells toxicity of GEM, AST as biomarker.
Figure 9:
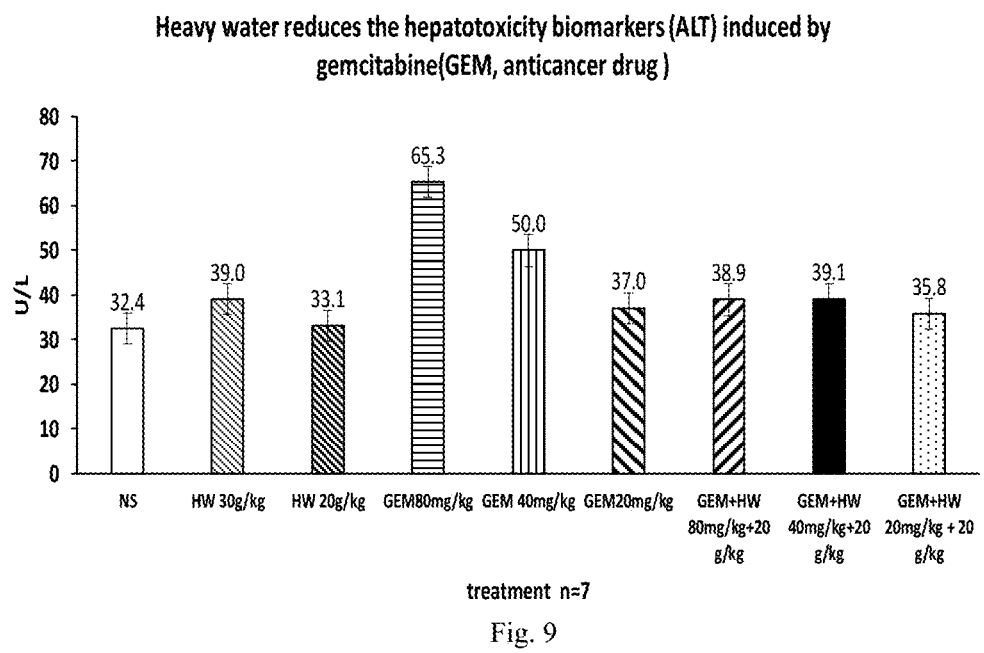
FIG. 9: Deuterium oxide reduced the liver cells toxicity of GEM, ALT as biomarker.

AST, ALT. No significant difference was found between deuterium oxide group and control group with regard to hepatotoxicity indices (FIG. 8, FIG. 9). GEM (80 and 40 mg/kg) significantly (P<005) increased the AST level, 174 U/L and 159 U/L, resp. and ALT level, 65 U/L and 50 U/L, resp. in the serum of mice. Compared with the GEM alone group, the AST and ALT levels significantly reduced to normal level (P<005) in the GEM plus deuterium oxide groups (FIG. 8, FIG. 9).

Discussion

In the present study, the GEM was significantly lower WBC in peripheral blood and increased AST, ALT in the serum, showed the toxicity of GEM to haematopoietic cells and liver cells. These results exhibited that GEM is toxic to haematopoietic cells and liver cells, and can cause liver damage.

But when deuterium oxide combined with GEM, it could significantly enhanced the recovery of the WBC, and lowered AST, ALT level, shown its function of toxicity-reducing for anti-tumor drug.

Statistic Analysis

A comparison of the data was carried out between the treatment groups and control group. The scale variable (expressed as mean±standard deviation) was proceeded by a Mann-Whitney test, and unpaired t-test). A two-side alpha of 0.05 was used for all tests.

Although some aspects of the present disclosure have been set forth and discussed herein, it would be appreciated by a person skilled in the art that modifications can be made to the above aspects without departing from the principle and spirit of the present disclosure. Therefore, the scope of the present disclosure is defined by the claims and equivalents therefore.

What is claimed is:

1. A method for treating cancer comprising administering a sterilized pharmaceutical solution, suspension, or emulsion, wherein the sterilized pharmaceutical solution, suspension, or emulsion comprises at least one antitumor drug, and deuterium oxide, and in the deuterium oxide, the isotope abundance of deuterium is 99.6 to 99.9% and wherein every 100 ml of the sterilized pharmaceutical solution, suspension, or emulsion contains 99.6 to 99.9 ml pure deuterium oxide; wherein the sterilized pharmaceutical solution, suspension, or emulsion has a pH adjusted to 5.0 to 7.0; and
wherein the solution, suspension or emulsion is for lavage and perfusion which is optionally hyperthermic, or,
wherein the solution, suspension, or emulsion is for injection.

2. The method according to claim 1, wherein the sterilized pharmaceutical solution, suspension or emulsion further comprises sodium chloride, the sterilized pharmaceutical solution, suspension or emulsion containing 0.1 g to 5 g sodium chloride per 100 ml, and having a pH adjusted to 7.0.

3. The method according to claim 1, wherein the sterilized pharmaceutical solution, suspension, or emulsion further comprises glucose, the sterilized pharmaceutical solution, suspension, or emulsion comprising 0.1 g to 50 g glucose per 100 ml, and having a pH adjusted to 5.5.

4. The method according to claim 1, wherein the sterilized pharmaceutical solution, suspension, or emulsion is a deuterium oxide solution, suspension, or emulsion comprising 0.9 g sodium chloride, 0.012 g potassium chloride and 0.024 g calcium chloride per 100 ml, and having a pH adjusted to 7.0.

5. The method according to claim 1, wherein the sterilized pharmaceutical solution, suspension, or emulsion further comprises hydroxyethyl starch, the sterilized pharmaceutical solution, suspension, or emulsion comprising 3 g to 8 g hydroxyethyl starch per 100 ml, and having a pH adjusted to 6.0 to 7.0.

6. The method according to claim 1, wherein the sterilized pharmaceutical solution, suspension, or emulsion further comprises hydroxypropyl-β-cyclodextrin (HP-β-CD), the sterilized pharmaceutical solution, suspension, or emulsion comprising 0.4 g to 10 g HP-β-CD per 100 ml, and having a pH adjusted to 5.0 to 7.0.

7. The method according to claim 1, wherein the sterilized pharmaceutical solution, suspension, or emulsion further comprises human albumin, the pharmaceutical solution, suspension, or emulsion comprising 5 to 25 g human albumin per 100 ml, and having a pH adjusted to 5.0 to 7.0.

8. The method according to claim 1, wherein the sterilized pharmaceutical solution, suspension, or emulsion further comprises polyethylene glycol (MW:300), the sterilized pharmaceutical solution, suspension, or emulsion comprising 1 g to 50 g polyethylene glycol per 100 ml, and having a pH adjusted to 5.0 to 7.0.

9. The method according to claim 1, wherein the sterilized pharmaceutical solution, suspension, or emulsion further comprises amino acid: L-proline 0.1 to 1.00 g, L-serine 0.1 to 1.00 g, L-alanine 0.1 to 2.00 g, L-isoleucine 0.1 to 3.52 g, L-leucine 0.1 to 4.90 g, L-aspartate 0.1 to 2.50 g, L-tyrosine 0.1 to 0.25 g, L-glutamate 0.1 to 0.75 g, L-phenylalanine 0.1 to 5.33 g, L-arginine 0.1 to 5.00 g, L-lysine 4.30 g, L-valine 0.1 to 3.60 g, L-threonine 0.1 to 2.5 g, L-histidine 0.1 to 2.5 g, L-tryptophan 0.1 to 0.9 g, L-methionine 0.1 to 2.25 g, L-cysteine 0.10 g, glycine 7.60 g, sorbitol 1 to 50.00 g, sodium bisulfite ($NaHSO_3$) 0.5 g and 1000 g deuterium oxide, per 1000 ml solution, suspension or emulsion, having a pH adjusted to 5.0 to 7.0.

10. The method according to claim 1, wherein the antitumor drug comprises 5-fluorouracil, gemcitabine, floxuridine, pemetrexed, raltitrexed, fludarabine, cytarabine, mitomycin, oxaliplatin, paclitaxel, bevacizumab, or mixtures thereof.

11. The method according to claim 1, wherein the dose of a solution, suspension, or emulsion for lavage and perfusion which is optionally hyperthermic is 5 to 6,000 ml/administration; the temperature of the solution, suspension, or emulsion for lavage and perfusion is 40° C. to 48±1° C. In the case wherein the solution, suspension, or emulsion for lavage and perfusion is hyperthermic; the solution, suspension, or emulsion for optionally hyperthermic lavage and perfusion, is used for perfusing and lavaging the thoracic cavity, the peritoneal cavity, the pelvic cavity, the bladder cavity, the buccal cavity, the nasal cavity, the enteric cavity, the uterine cavity, or the skin of mammal having a tumor.

12. The method according to claim 1, wherein the solution, suspension, or emulsion for injection is for intravenous injection, intra-arterial injection, intrathecal injection, intratumoral injection, or peritumoral injection, RJ the dose of the solution, suspension, or emulsion for injection is 1 ml/kg to 20 ml/kg.

* * * * *